United States Patent
Dennis et al.

(10) Patent No.: US 10,720,143 B2
(45) Date of Patent: Jul. 21, 2020

(54) SOUND EMITTING DEVICE

(71) Applicant: Marpac, LLC, Wilmington, NC (US)

(72) Inventors: Jason Aaron Dennis, Wilmington, NC (US); Jessica Hurwit, Princeton, NJ (US)

(73) Assignee: Marpac, LLC, Wilmington, NC (US)

( * ) Notice: Subject to any disclaimer, the term of this patent is extended or adjusted under 35 U.S.C. 154(b) by 0 days.

(21) Appl. No.: 16/268,771

(22) Filed: Feb. 6, 2019

(65) Prior Publication Data
US 2019/0172439 A1    Jun. 6, 2019

Related U.S. Application Data

(63) Continuation-in-part of application No. 29/578,675, filed on Sep. 23, 2016, now Pat. No. Des. 847,373.

(60) Provisional application No. 62/626,952, filed on Feb. 6, 2018.

(51) Int. Cl.
| | |
|---|---|
| *G10K 11/178* | (2006.01) |
| *G10L 19/012* | (2013.01) |
| *G10K 11/175* | (2006.01) |
| *A61F 11/00* | (2006.01) |
| *G10K 15/04* | (2006.01) |

(52) U.S. Cl.
CPC ........ *G10K 11/17855* (2018.01); *A61F 11/00* (2013.01); *G10K 11/175* (2013.01); *G10K 15/04* (2013.01); *G10L 19/012* (2013.01); *G10K 2210/12* (2013.01)

(58) Field of Classification Search
CPC .......... G10K 11/17855; G10K 11/175; G10K 15/04; G10K 2210/12; A61F 11/00; G10L 19/012
See application file for complete search history.

(56) References Cited

U.S. PATENT DOCUMENTS

2017/0046115 A1*  2/2017  Rahardjo ............... G06F 3/162

FOREIGN PATENT DOCUMENTS

WO     WO-2017035388 A2 *  3/2017  ............ G10K 15/04

\* cited by examiner

*Primary Examiner* — Mark Fischer
(74) *Attorney, Agent, or Firm* — E. Eric Mills; Nexsen Pruet, PLLC

(57) ABSTRACT

A sound making device and system for generating white noise is disclosed. The sound making device generally includes a substantially dome-shaped device that includes an outer acoustic shell and an inner acoustic shell mounted atop a base tray. Both the outer acoustic shell and inner acoustic shell have slots (or openings) that overlap to create apertures through which rushing air can pass. The amount of slot overlap is variable. Further, a variable speed fan is arranged inside the outer acoustic shell and inner acoustic shell for forcing airflow out of the apertures. The sound making device also includes a controller and user interface for adjusting the speed of the fan. Further, a sound making system is provided that includes the sound making device in combination with a mobile app.

19 Claims, 25 Drawing Sheets

SOUND EMITTING DEVICE

CROSS-REFERENCE TO RELATED APPLICATIONS

The presently disclosed subject matter is related to and claims priority to U.S. Design patent application No. 29/578,675 entitled "Sound Emitting Device" filed on Sep. 23, 2016 and U.S. Provisional Patent Application No. 62/626,952 entitled "Sound Emitting Device" filed on Feb. 6, 2018; the entire disclosures of which are incorporated herein by reference.

TECHNICAL FIELD

The presently disclosed subject matter relates generally to sound making devices and more particularly to a sound making device and system for generating white noise.

BACKGROUND

White noise is created by a continuum of frequencies equally distributed over the whole hearing range. In healthcare applications, white noise is used to treat hyperacusis, an increased sensitivity to normal environmental sounds, or to camouflage the annoyance caused by tinnitus, a ringing in the ear occurring without any stimulus.

White noise is also used to mask background noises in the office, or to aid in sleep. For example, sound conditioners are known to camouflage undesirable noise in the environment by generating white noise privacy. These devices can be standalone units that sit on a night stand or the like for use by individuals at night to aid sleep. Sound conditioners can be used to promote healthier lifestyles by successfully improving sleep patterns and/or reducing sleep related problems such as insomnia and anxiety, which may result in increased energy and focus throughout the day.

SUMMARY

A sound making device for generating white noise is provided and generally includes a substantially dome-shaped device that includes an outer acoustic shell and an inner acoustic shell mounted atop a base tray. Both the outer acoustic shell and inner acoustic shell have slots (or openings) that overlap to create apertures through which rushing air can pass. The amount of slot overlap is variable. Further, a variable speed fan is arranged inside the outer acoustic shell and inner acoustic shell for forcing airflow out of the apertures. The sound making device also typically includes a controller and user interface for adjusting the speed of the fan. The controller also typically provides a communications means. In the presently disclosed sound making device, the sound is produced mechanically using the fan.

In one example, the sound making device may include an enclosure housing having an outer acoustic shell and an inner acoustic shell mounted atop a base tray, the outer acoustic shell having a set of outer acoustic shell slots and the inner acoustic shell having a set of inner acoustic shell slots, the outer acoustic shell slots and the inner acoustic shell slots overlapping to form a set of apertures through which air can pass; a fan assembly inside the enclosure including a variable speed fan and a fan motor for forcing the air out of the apertures; and a controller and a user interface assembly for controlling the speed of the variable speed fan. The enclosure may be substantially dome-shaped. Namely, the outer acoustic shell may be dome-shaped, and the inner acoustic shell may be dome-shaped.

In one example, the outer acoustic shell may be rotatable with respect to the inner acoustic shell. That is, the inner acoustic shell may be fixed, and the outer acoustic shell may be rotatable to varying positions around the inner acoustic shell. The shape of each aperture of the set of apertures is adjustable according to the position of the rotatable outer acoustic shell in relation to the fixed inner acoustic shell. The outer acoustic shell may include a user interface opening for receiving the user interface assembly and a set of large-diameter alignment features and a set of small-diameter alignment features around the inner surface of the outer acoustic shell. The inner acoustic shell may include a set of large-width alignment slots and a set of small-width alignment slots around the top of the inner acoustic shell, the set of large-width alignment slots and the set of large-diameter alignment features being slideably engaged, and the set of small-width alignment slots and the set of small-diameter alignment features being slideably engaged.

In one example, the set of outer acoustic shell slots may be arranged around the sides of the outer acoustic shell and angled in one direction, wherein the set of inner acoustic shell slots are arranged around the side of the inner acoustic shell and angled in a direction opposite to the one direction, the set of outer acoustic shell slots and the set of inner acoustic shell slots being in a cross configuration. Each slot of the set of outer acoustic shell slots may be a substantially uniformly shaped slot, and each slot of the set of inner acoustic shell slots may be a tapered slot.

The user interface assembly of one example may include an inner portion arranged with respect to user interface support ring surrounding the inner portion, and a user interface circuit board, the inner portion supporting a power button, and the user interface support ring supporting an increase volume button and a decrease volume button. The inner acoustic shell may include an upper receiver portion for supporting the user interface assembly, the user interface support ring being mounted above and coupled to the receiver portion, the user interface circuit board being mounted below and coupled to the receiver portion, the user interface circuit board having a first pushbutton switch corresponding to the power button, a second pushbutton switch corresponding to the increase volume button, and a third pushbutton switch corresponding to the decrease volume button.

In one example, the fan assembly may be held by the base tray, the base tray may include a motor mount, the fan assembly may include a motor support for mounting to the motor mount and for holding the fan motor, the fan motor having a motor shaft, the variable speed fan having a fan blade, wherein the fan blade is mounted on the motor shaft. Also, a power circuit board may be provided for receiving DC voltage and for voltage regulation function for powering the fan motor and the user interface assembly, the power circuit board including a power port, the power circuit board being installed in the base tray, and the base tray including an opening along an outer edge of the base trade to provide access to the power port. The outermost edge of the fan blade may be a distance D from the inside surface of the inner acoustic shell, and the fan blade may be located at a height with respect to the set of inner acoustic shell slots.

The present invention also provides a sound making system for generating white noise. In one example, the sound making system includes a sound making device having an enclosure housing having an outer acoustic shell and an inner acoustic shell mounted atop a base tray, the outer acoustic shell having a set of outer acoustic shell slots and the inner acoustic shell having a set of inner acoustic shell slots, the outer acoustic shell slots and the inner acoustic shell slots overlapping to form a set of apertures through which air can pass, a fan assembly inside the enclosure including a variable speed fan and a fan motor for forcing the air out of the apertures, a controller to manage the overall operations of the sound making device, a user interface assembly for manual operation of the sound making device, and a power source for powering the sound making device; and a mobile app for using the sound making device. The sound making system may further include a communications interface for communicating with the mobile app, and a voice control for communicating with a voice-based personal assistant. The mobile app may be adapted to exchange information between the sound making device and the computing device.

BRIEF DESCRIPTION OF THE DRAWINGS

Figure 1:
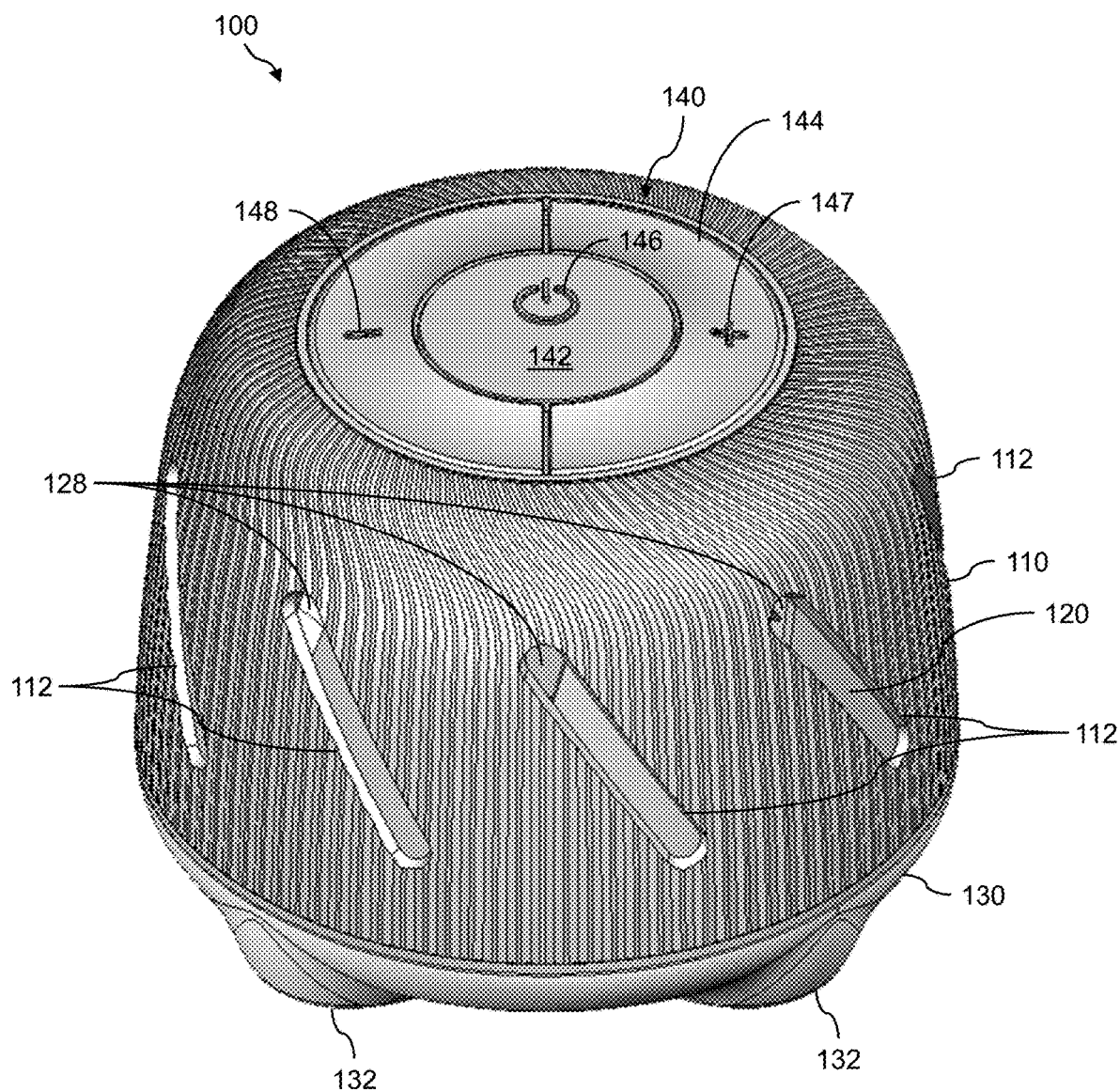
Figure 2:
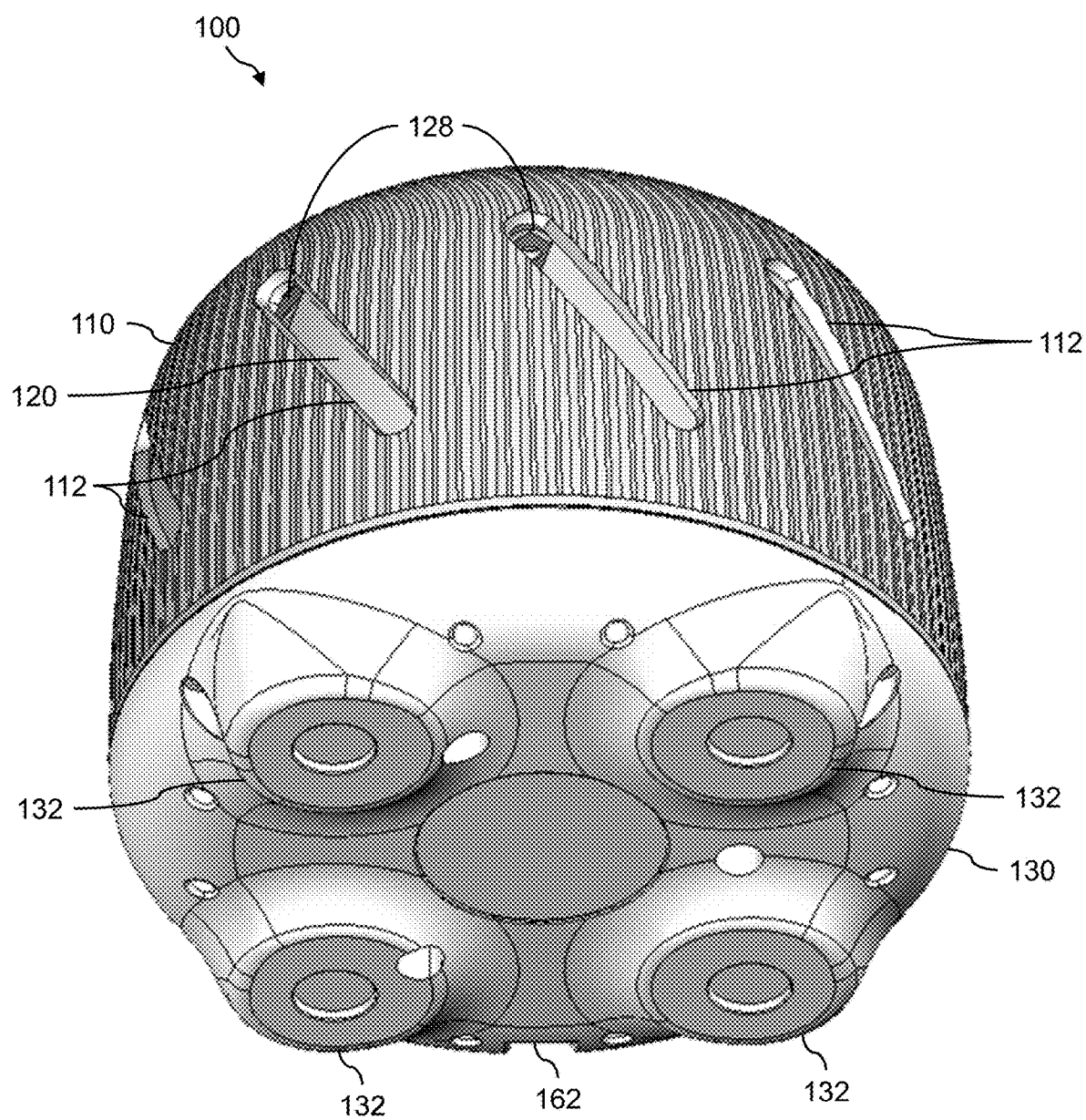
Figure 3:
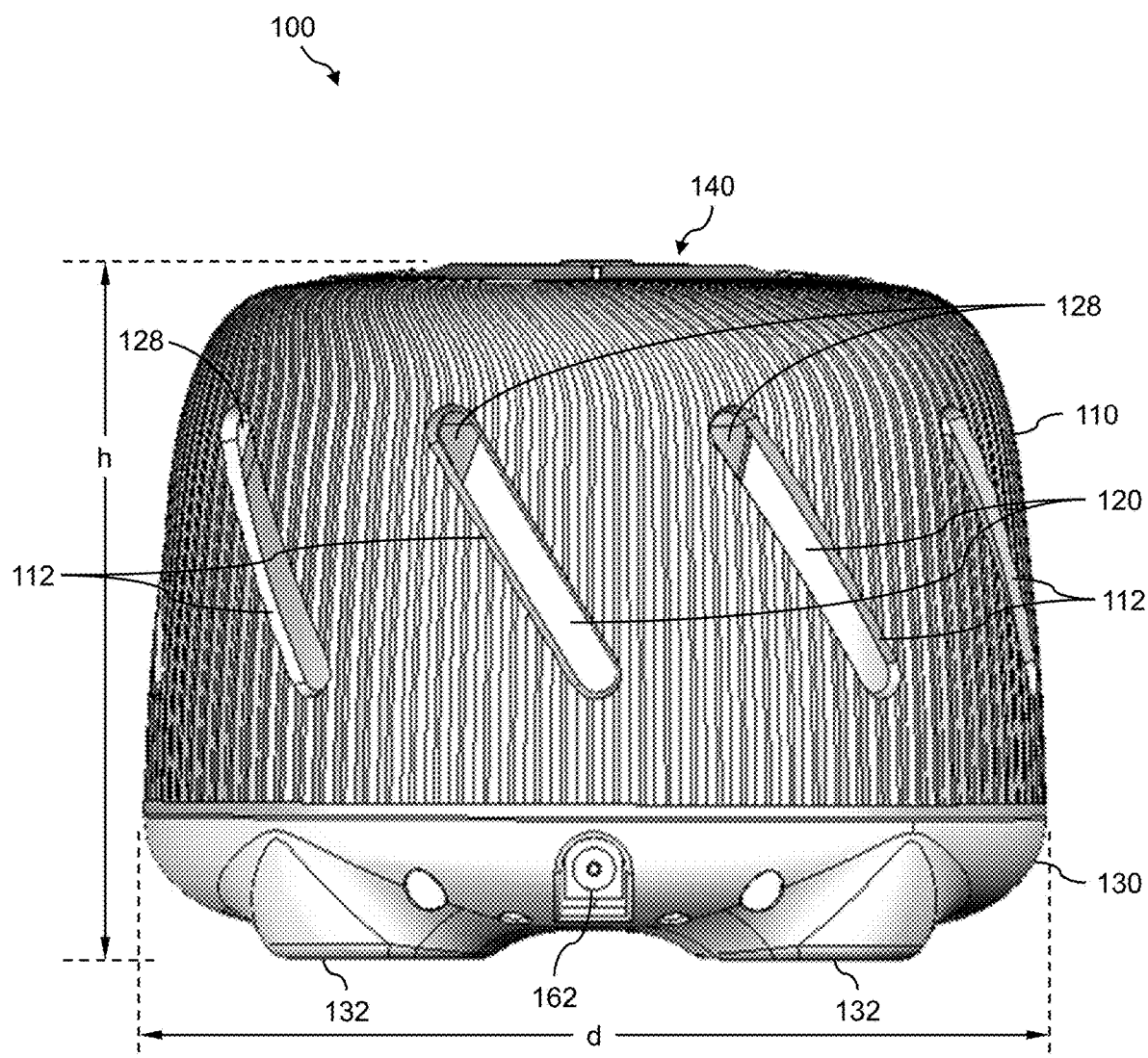
Figure 4:
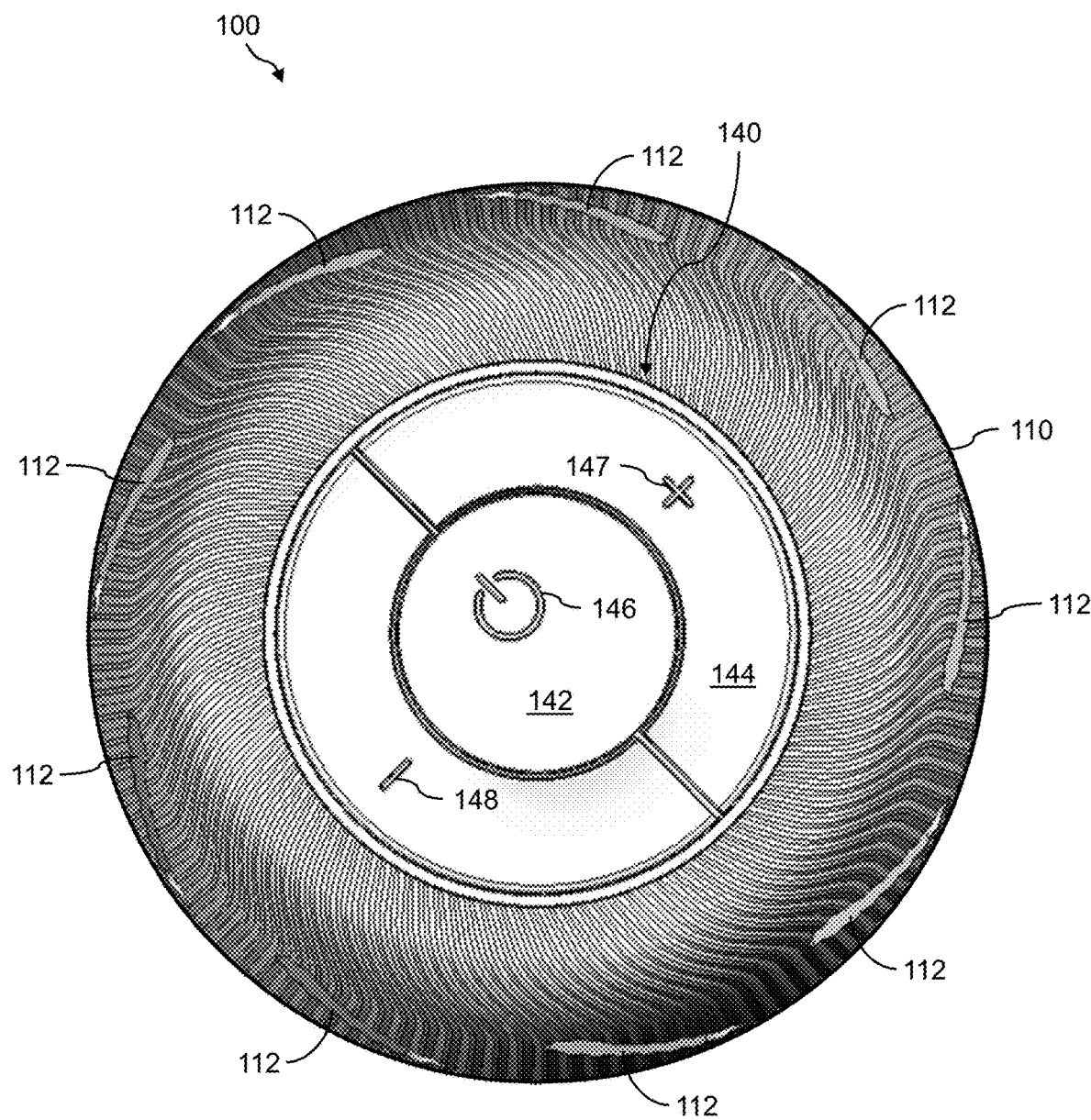
Figure 5:
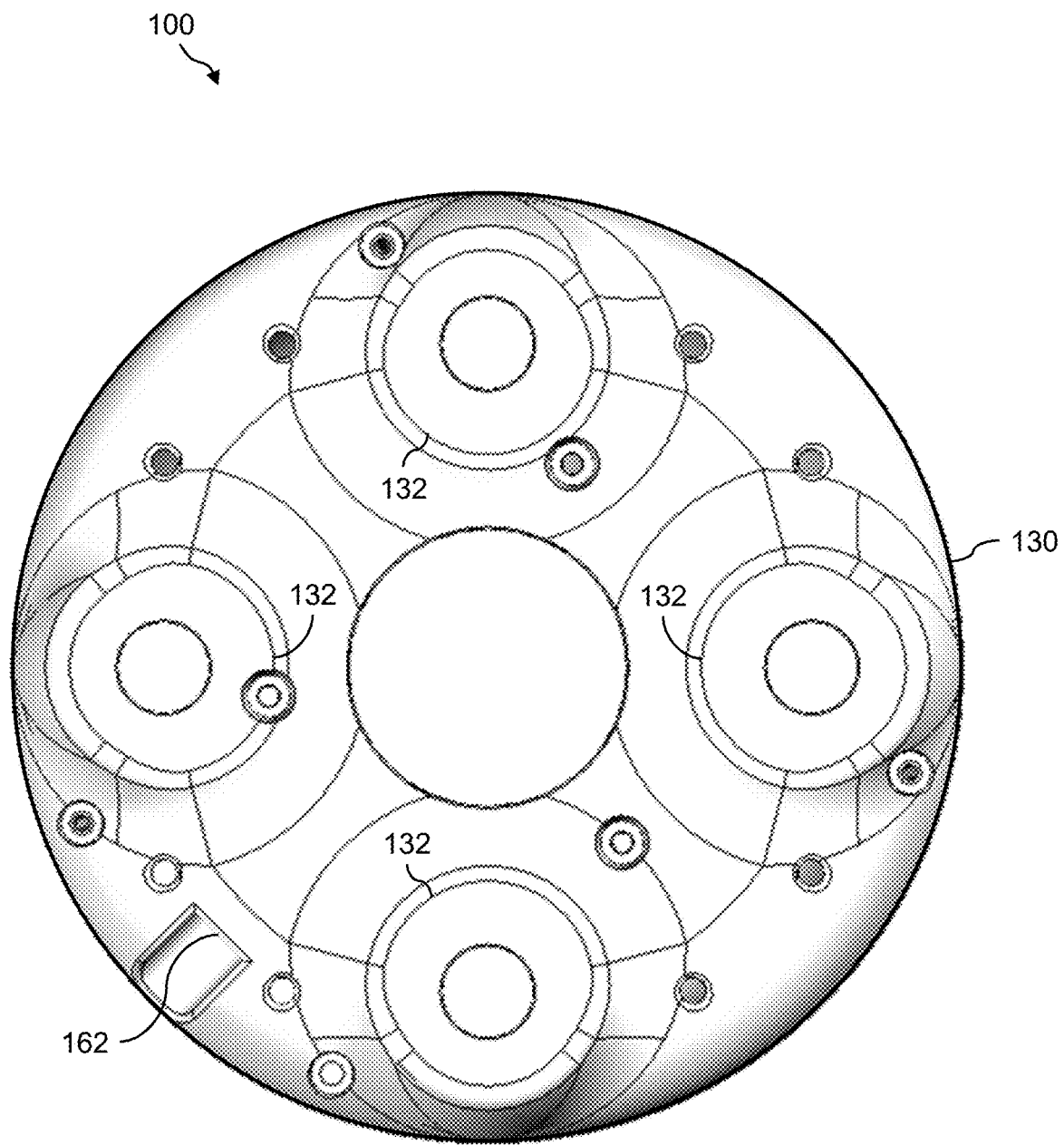
Figure 6:
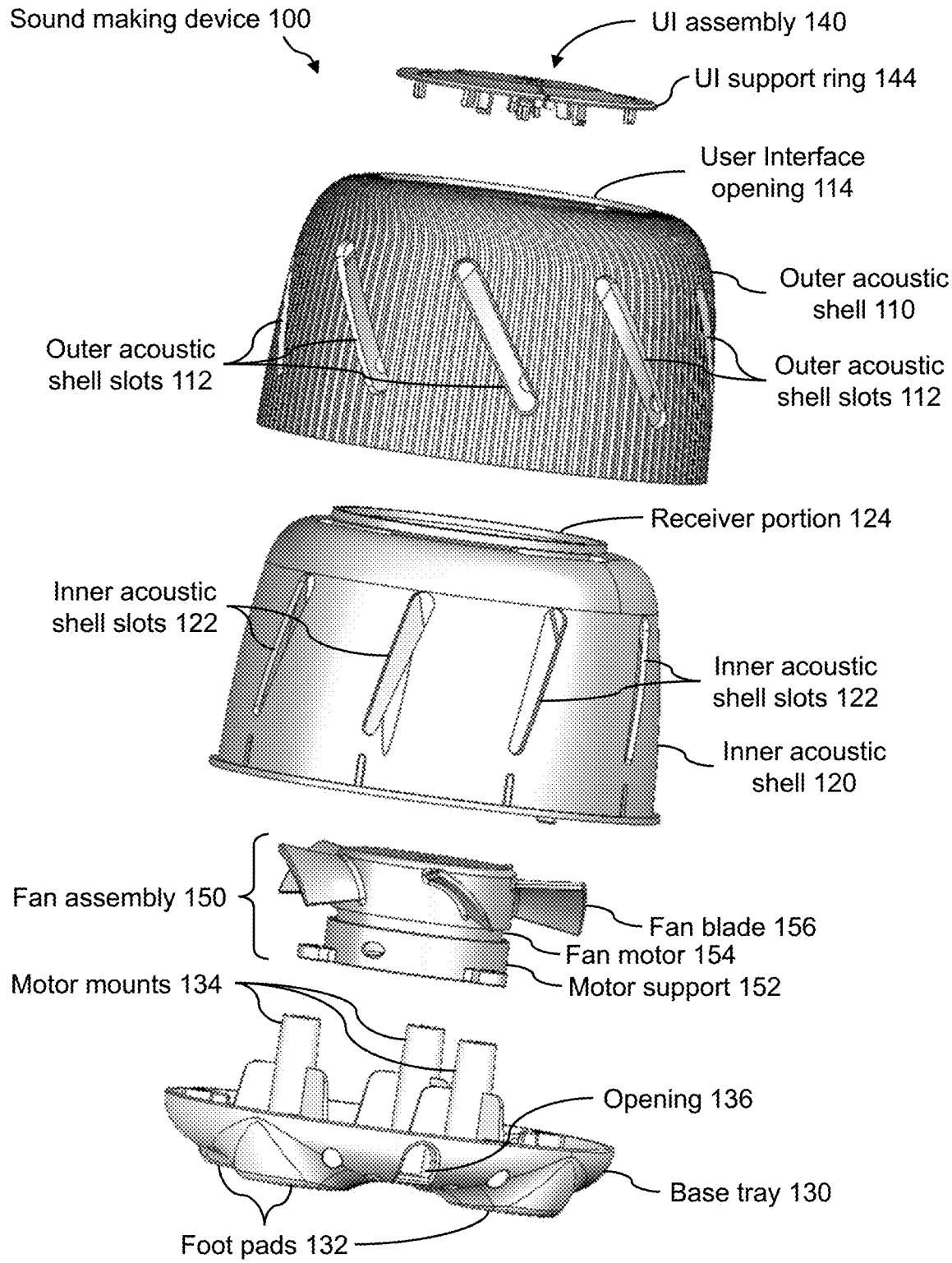
Figure 7:
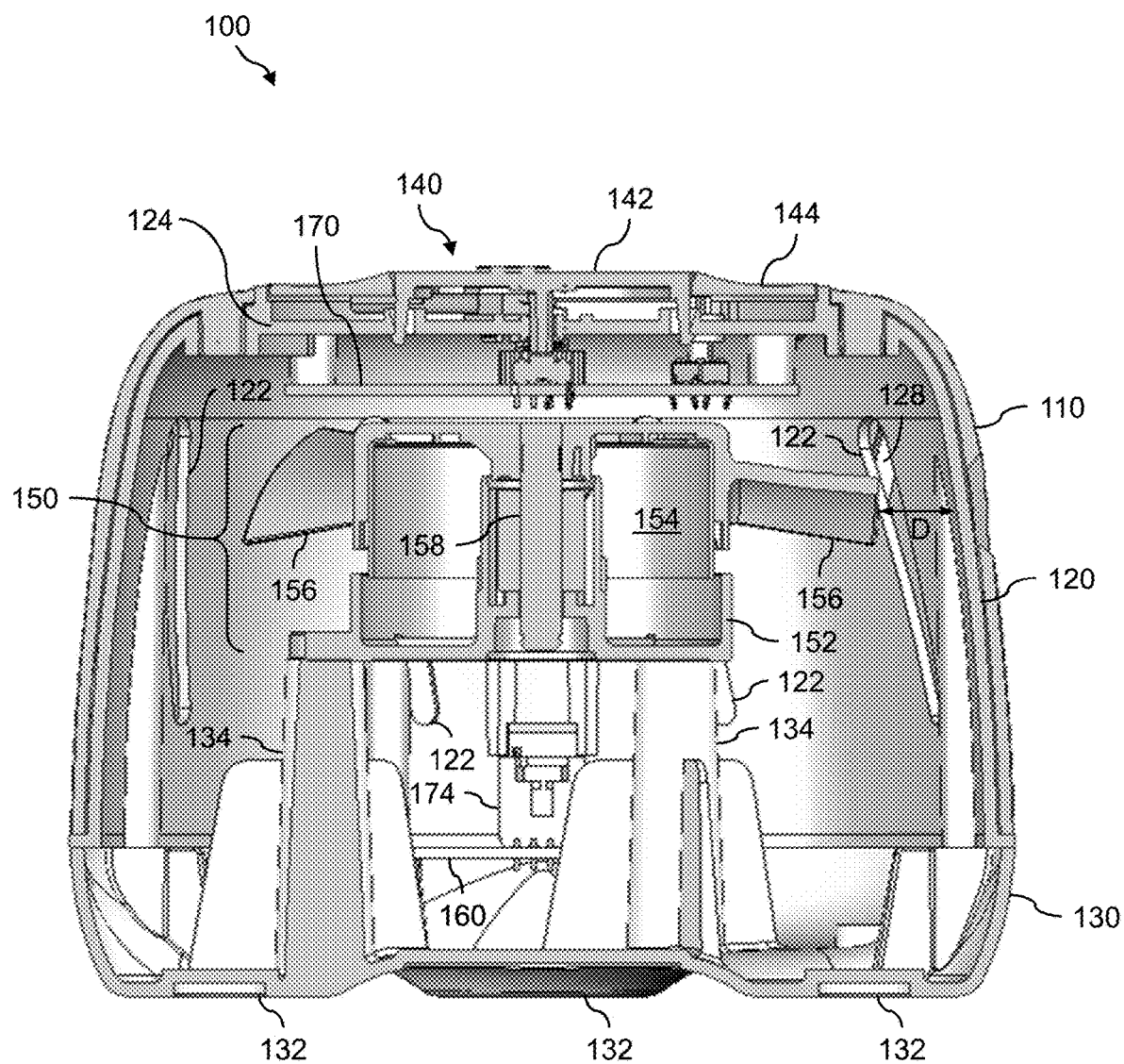
Figure 8:
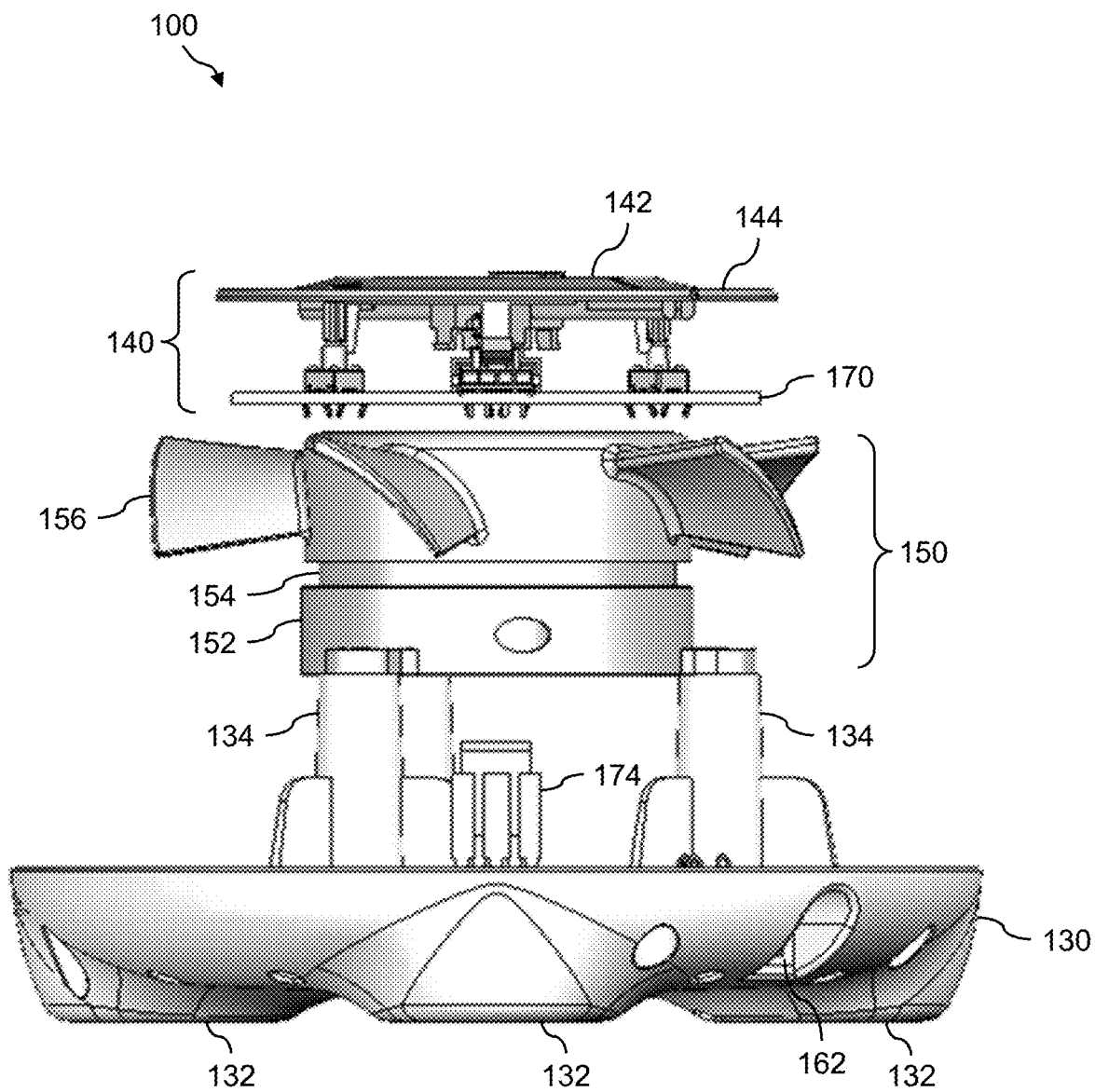
Figure 9:
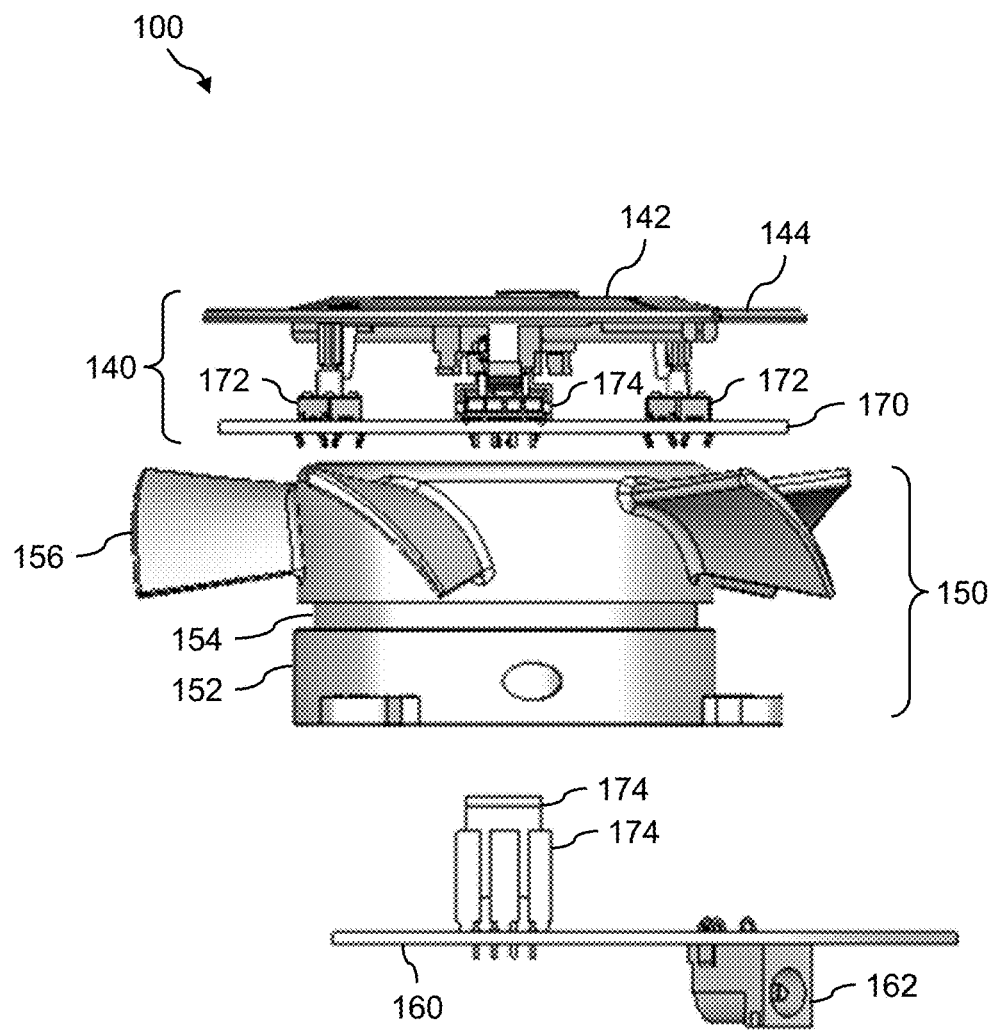
Figure 10:
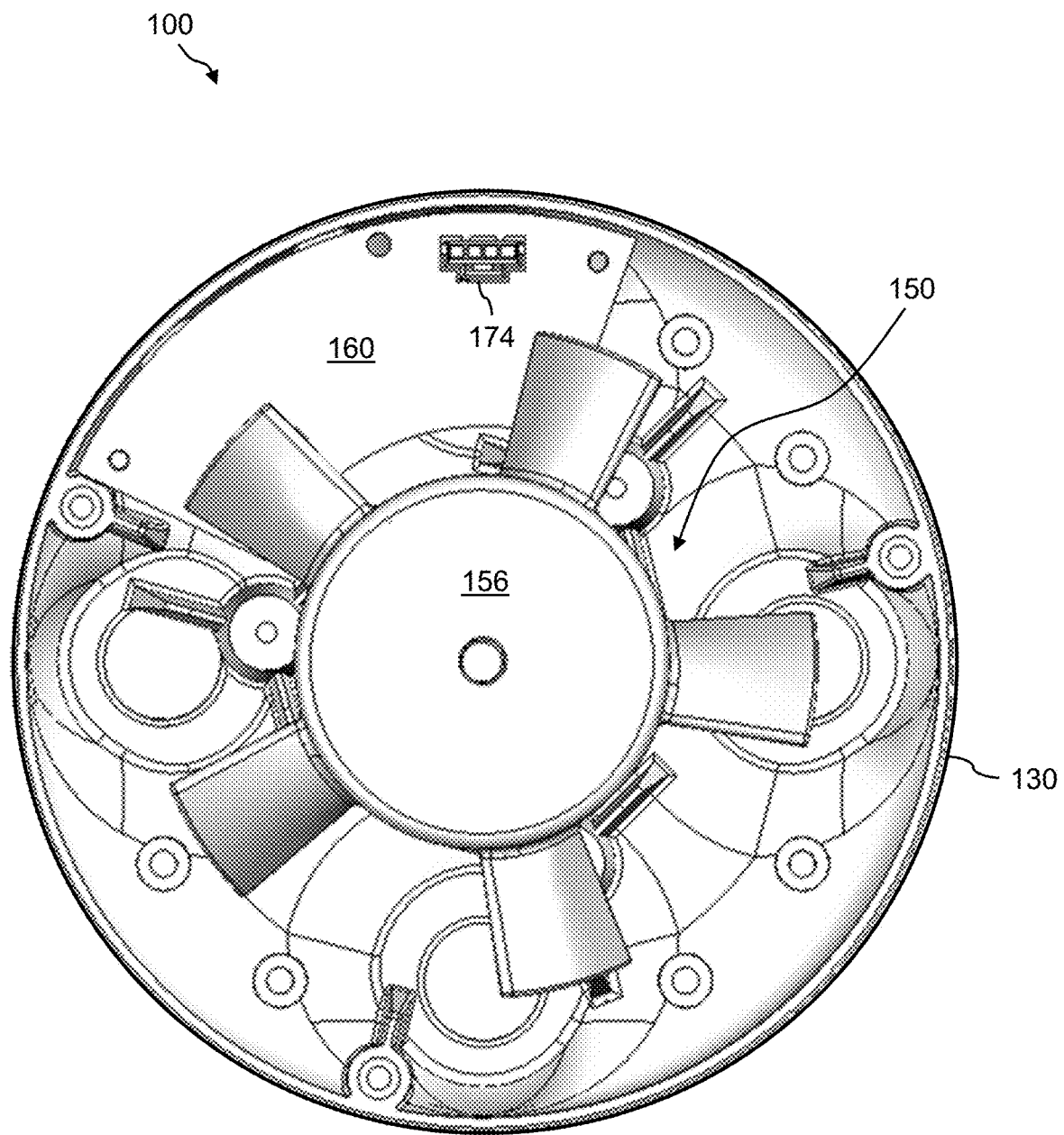
Figure 11:
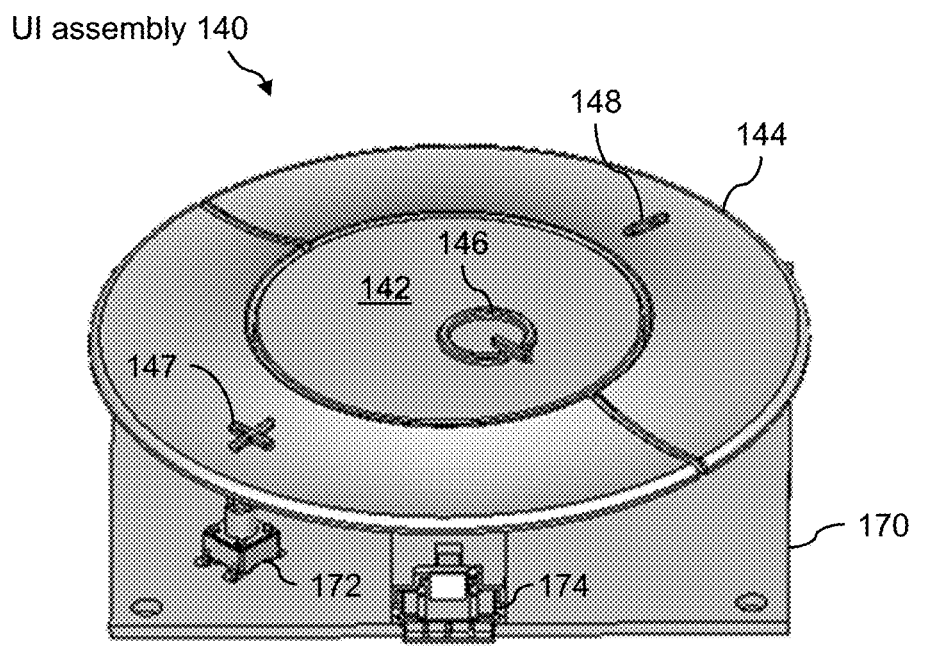
Figure 11:
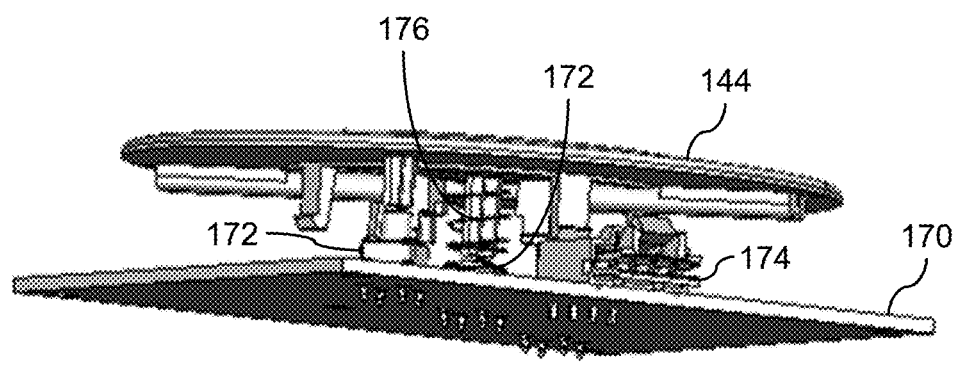
Figure 12:
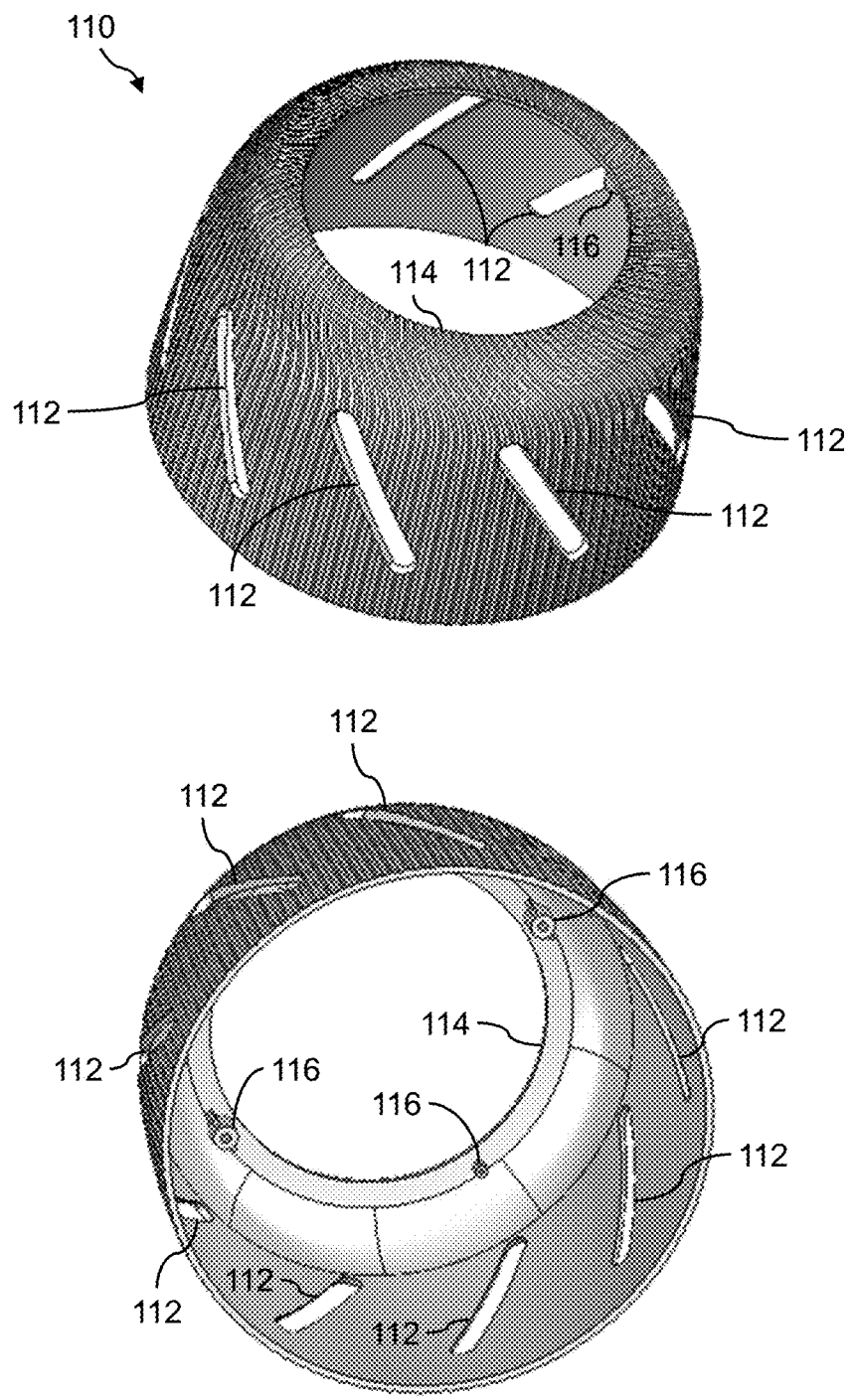
Figure 13:
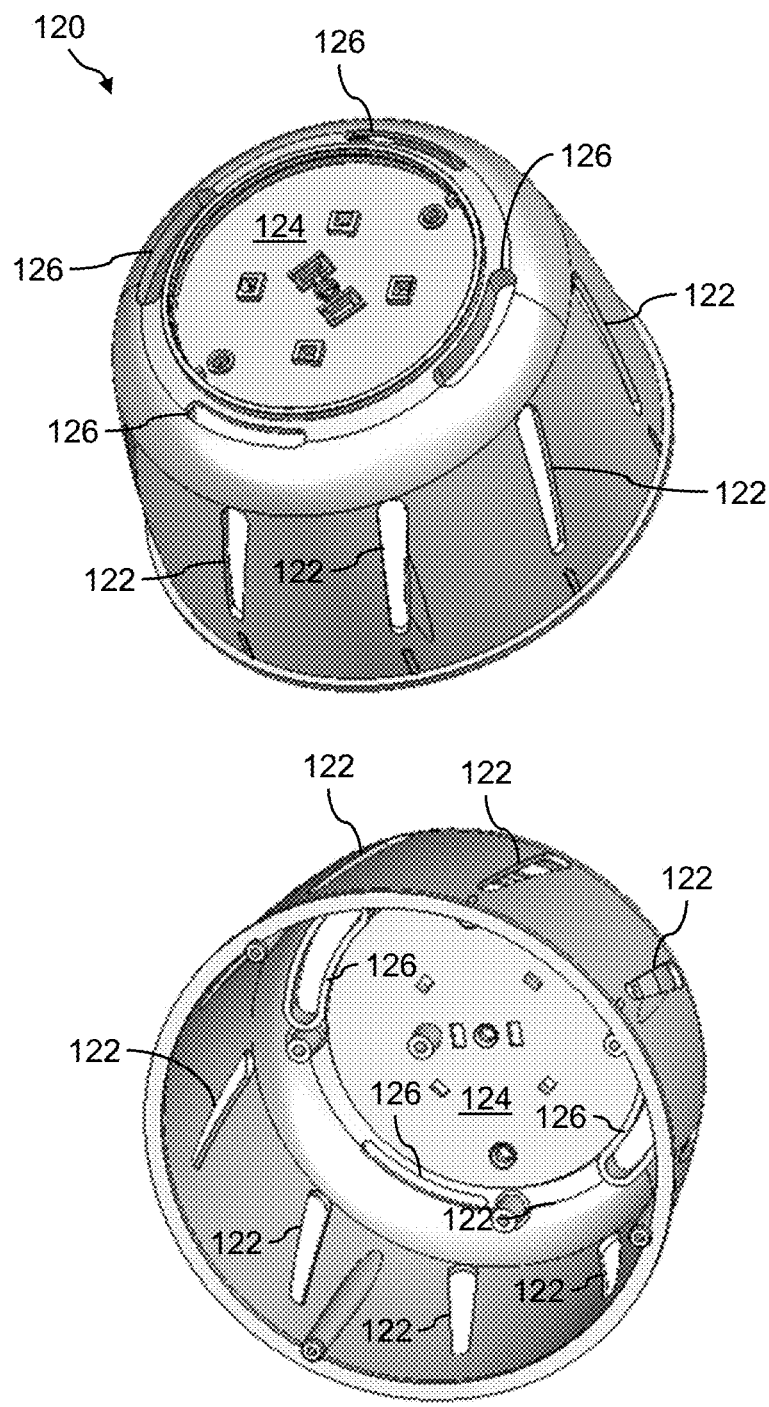
Figure 14:
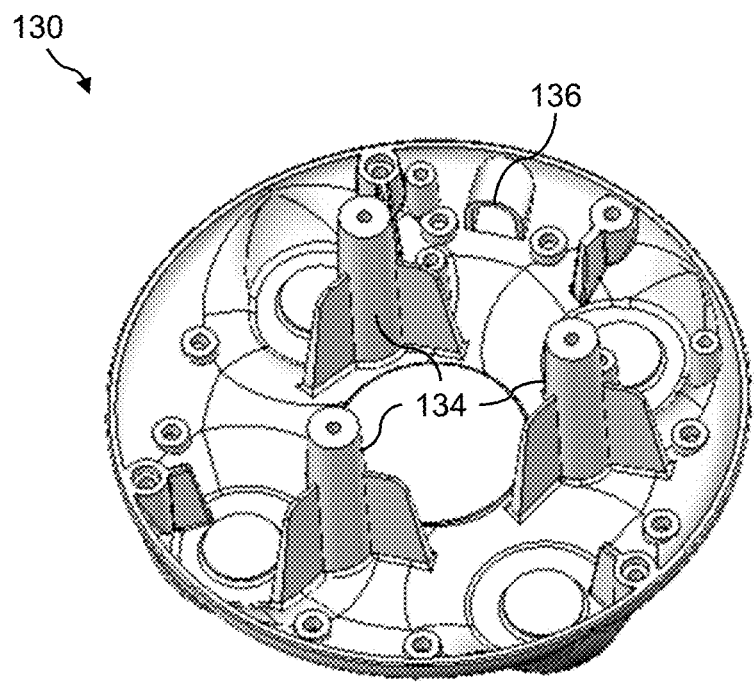
Figure 14:
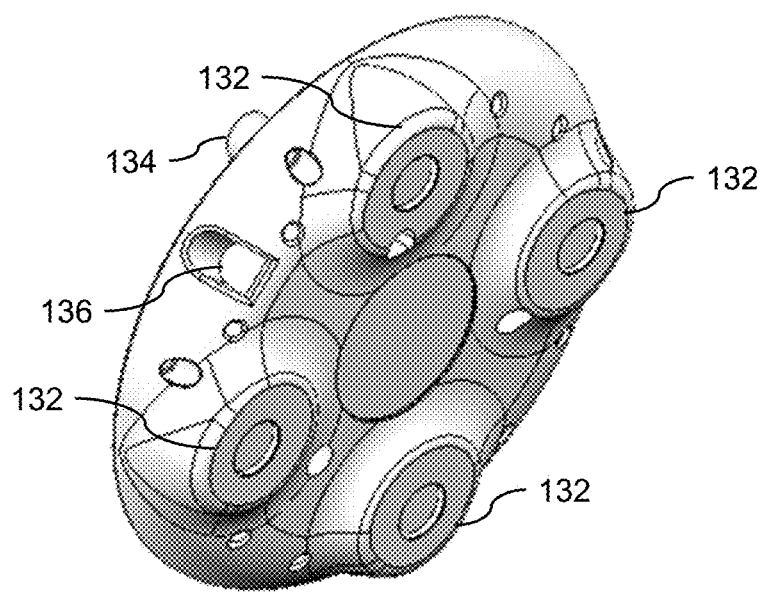
Figure 15:
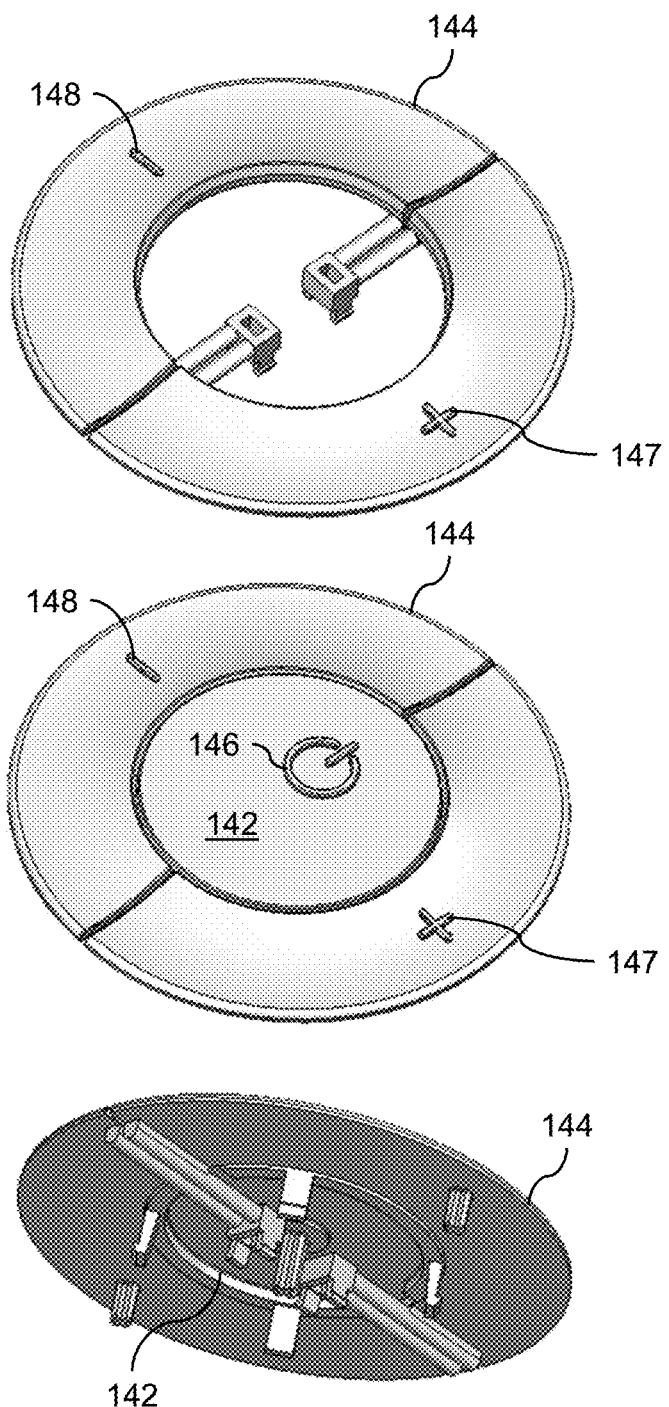
Figure 16A:
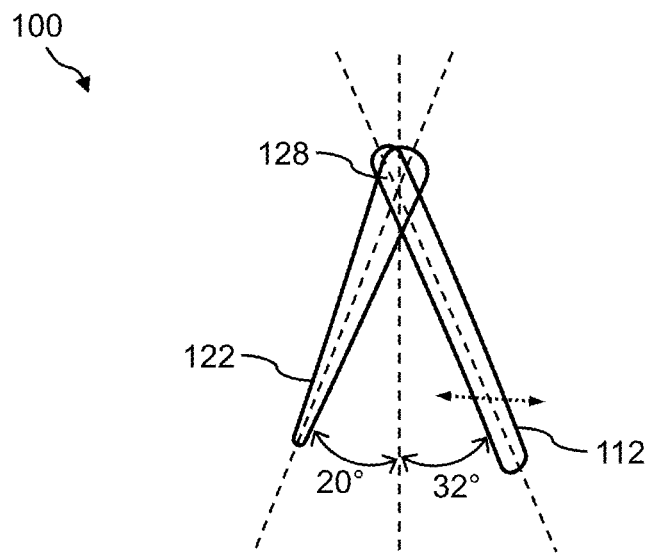
Figure 16B:
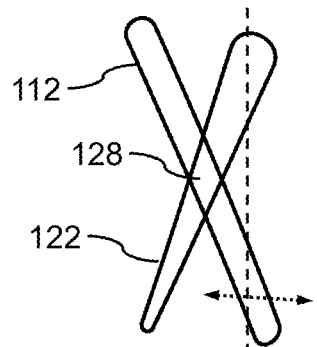
Figure 16C:
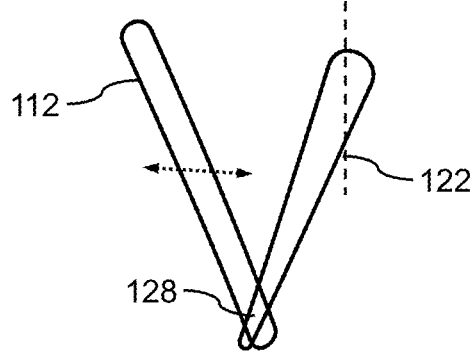
Figure 17:
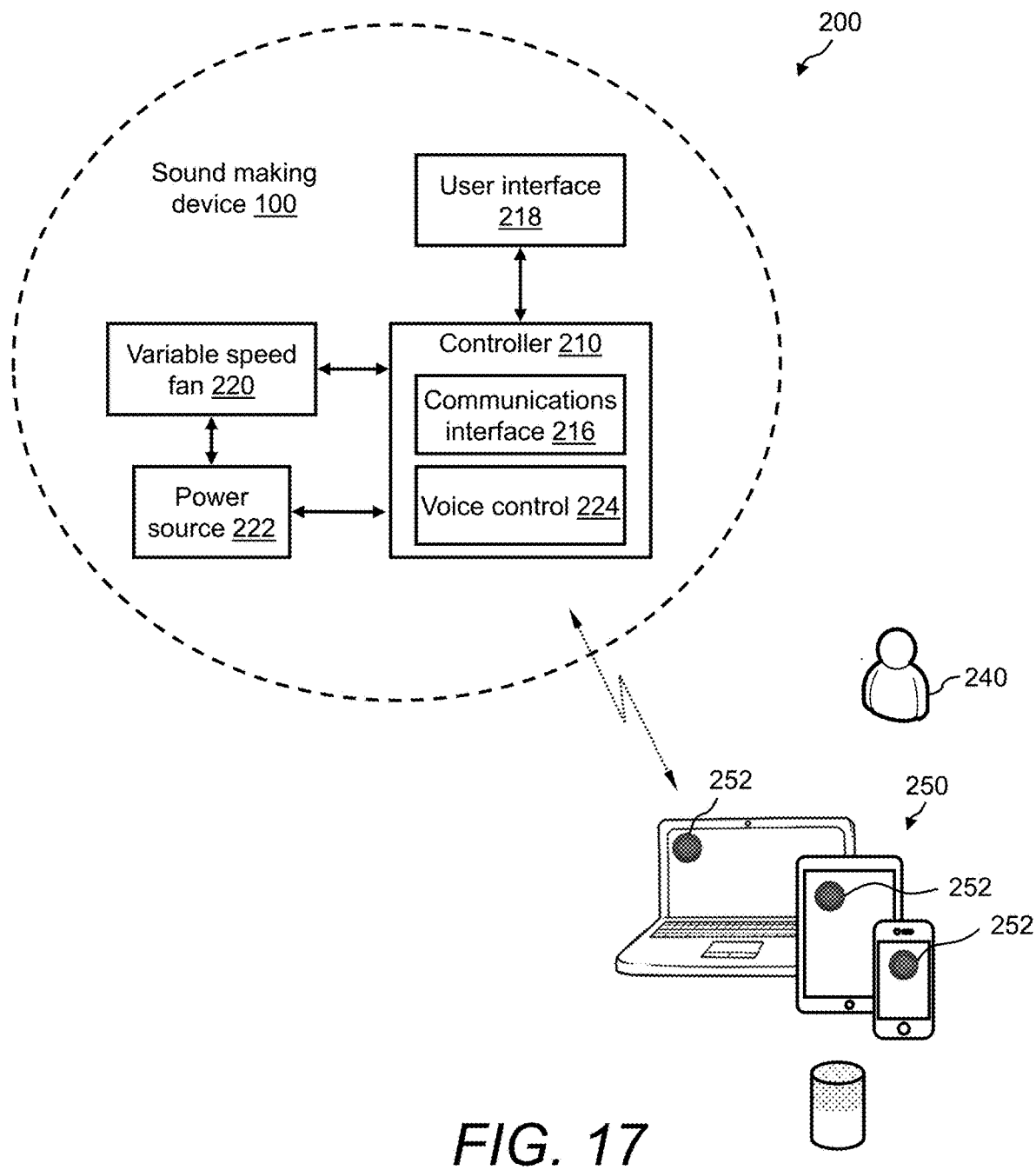

Having thus described the presently disclosed subject matter in general terms, reference will now be made to the accompanying drawings, which are not necessarily drawn to scale, and wherein:

FIG. 1 and FIG. 2 illustrate a top perspective view and a bottom perspective view, respectively, of an example of the presently disclosed sound making device;

FIG. 3, FIG. 4, and FIG. 5 illustrate a side view, a top view, and a bottom view, respectively, of the sound making device shown in FIG. 1 and FIG. 2;

FIG. 6 and FIG. 7 illustrate a partial exploded view and a cross-sectional view, respectively, of the sound making device shown in FIG. 1 through FIG. 5;

FIG. 8, FIG. 9, and FIG. 10 illustrate side views and a top view, respectively, showing more details of the inner components of the presently disclosed sound making device;

FIG. 11 illustrates perspective views showing more details of the user interface assembly of the presently disclosed sound making device;

FIG. 12 illustrates perspective views of an example of an outer acoustic shell of the presently disclosed sound making device;

FIG. 13 illustrates perspective views of an example of an inner acoustic shell of the presently disclosed sound making device;

FIG. 14 illustrates perspective views of an example of a base tray of the presently disclosed sound making device;

FIG. 15 illustrates various views of an example of a user interface of the presently disclosed sound making device;

FIG. 16A, FIG. 16B, and FIG. 16C illustrate the variable overlap region of the outer acoustic shell slots and the inner acoustic shell slots of the presently disclosed sound making device;

FIG. 17 illustrates a block diagram of an example of a sound making system that includes the presently disclosed sound making device in combination with a mobile app; and FIG. 18 through FIG. 25 is a series of views showing the deconstruction of the presently disclosed sound making device and incrementally revealing the components thereof.

DETAILED DESCRIPTION

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a sound making device and system for generating white noise. Namely, the presently disclosed sound making device provides a sound conditioner, also called a white noise sound machine, for providing white noise privacy.

The sound making device generally consists of a substantially dome-shaped device that includes an outer acoustic shell and an inner acoustic shell mounted atop a base tray. Both the outer acoustic shell and inner acoustic shell have slots (or openings) that overlap to create apertures through which rushing air can pass. The amount of slot overlap is variable. Further, a variable speed fan is arranged inside the outer acoustic shell and inner acoustic shell for forcing airflow out of the apertures. The sound making device also typically includes a controller and user interface for adjusting the speed of the fan. The controller also typically provides a communications means. In the presently disclosed sound making device, the sound is produced mechanically using the fan.

With respect to producing sound mechanically, the outer acoustic shell is rotatable with respect to the inner acoustic shell for changing the relationship of the outer slots that overlap with the inner slots and thereby adjusting the size (i.e., area) and/or shape of the apertures. In operation, rushing air passes through the apertures that are created at the overlapping regions of the outer acoustic shell slots and the inner acoustic shell slots, whereby adjusting the size and/or shape of the apertures (i.e., adjusting the outer acoustic shell slots with respect to the inner acoustic shell slots) affects the loudness and/or tone of the sound. Accordingly, the sound making device is a sound emitting machine that produces a soothing white noise, wherein the unique sound frequencies are reached through the acoustically engineered combination of the DC motor, fan blades, and enclosure housing.

Further, a sound making system is provided that includes the presently disclosed sound making device in combination with a mobile app.

FIG. 1 and FIG. 2 illustrate a top perspective view and a bottom perspective view, respectively, of an example of the presently disclosed sound making device 100. FIG. 3, FIG. 4, and FIG. 5 illustrate a side view, a top view, and a bottom view, respectively, of the sound making device 100 shown in FIG. 1 and FIG. 2. FIG. 6 and FIG. 7 illustrate a partial exploded view and a cross-sectional view, respectively, of the sound making device 100 shown in FIG. 1 through FIG. 5.

Referring now to FIG. 1 through FIG. 7, the presently disclosed sound making device 100 is a substantially dome-shaped white noise sound machine. The sound making device 100 includes a dome-shaped outer acoustic shell 110 and a dome-shaped inner acoustic shell 120, both arranged with respect to a base tray 130. The base tray 130 includes, for example, four foot pads 132 by which the sound making device 100 can be rested on a surface and a set of motor mounts 134 for holding a fan assembly 150. The outer acoustic shell 110 includes a set of slots or openings (e.g., nine outer acoustic shell slots 112) arranged around the sides thereof. Similarly, the inner acoustic shell 120 includes a set of slots or openings (e.g., nine inner acoustic shell slots 122) arranged around the sides thereof. However, in the sound making device 100, the number of outer acoustic shell slots 112 and inner acoustic shell slots 122 is not limited to nine. Any number of slots can be provided, albeit the number of outer acoustic shell slots 112 and inner acoustic shell slots 122 is the same. For example, the sound making device 100 can include 3 to 9 outer acoustic shell slots 112 and a corresponding 3 to 9 inner acoustic shell slots 122.

The sound making device 100 further includes a user interface (UI) assembly 140. The UI assembly 140 typically includes a substantially circular-shaped inner portion 142 arranged with respect to a UI support ring 144 that surrounds the inner portion 142. The inner portion 142 of the UI assembly 140 supports a power (on/off) button 146. The UI support ring 144 of the UI assembly 140 supports an increase volume button 147 and a decrease volume button 148. The UI assembly 140 further includes a UI circuit board 170 (see FIG. 7). Further, the upper portion of the outer acoustic shell 110 includes a UI opening 114 (see FIG. 6 and FIG. 12) for receiving the UI assembly 140. Additionally, the upper portion of the inner acoustic shell 120 includes a receiver portion 124 (see FIG. 6 and FIG. 13) for supporting the UI assembly 140. Namely, the UI support ring 144 is mounted above and coupled to the receiver portion 124, such as by snap-fitting features, and the UI circuit board 170 is mounted below and coupled to the receiver portion 124 of the inner acoustic shell 120.

With reference to FIGS. 6 and 7, the fan assembly 150 is mounted atop the motor mounts 134 of the base tray 130 and housed in the space within the outer acoustic shell 110 and the inner acoustic shell 120. The fan assembly 150 includes a motor support 152 for mounting to the motor mounts 134 of the base tray 130 and for holding a fan motor 154. In one example, the motor support 152 is coupled to the motor mounts 134 via screws (not shown). A fan blade 156 is mounted on a motor shaft 158 of the fan motor 154. A circuit board 160 is installed in the base tray 130. The circuit board 160 is the power board for sound making device 100. The sound making device 100 is powered by a DC adaptor (not shown). Accordingly, the circuit board 160 includes a power port 162 for receiving the DC adaptor connector (not shown). In one example, an opening 136 in the outer edge of the base tray 130 provides access to the power port 162.

Generally, the circuit board 160 receives a DC voltage input and then provides a standard voltage regulation function for powering the fan motor 154 and the UI circuit board 170. The UI circuit board 170 is the control board of the sound making device 100 that supports the functions of the UI assembly 140. More details of the UI assembly 140 are shown and described hereinbelow with reference to FIG. 8, FIG. 9, FIG. 11, and FIG. 20 through FIG. 25.

Referring now to FIG. 3, the presently disclosed sound making device 100 has a height h and a diameter d. In one example, the sound making device 100 has a height h of about 4.22 inches and a diameter d of about 5.51 inches.

Referring now to FIG. 7, there is a distance D between the outermost edge of the fan blade 156 and the inside surface of the inner acoustic shell 120. In one example, the distance D can be from about 0.25 inches to about 0.625 inches.

Further, the location (i.e., the height) of the fan blade 156 (after installation of the fan motor 154 in the inner acoustic shell 120) can be from about midway to about the top of the inner acoustic shell slots 122. The location (i.e., the height) of the fan blade 156 with respect to the inner acoustic shell slots 122 is key to the tone control of the sound making device 100. For example, locating the fan blade 156 about midway of the inner acoustic shell slots 122 results in lower volume and less tone control range. By contrast, locating the fan blade 156 near the top of the inner acoustic shell slots 122 results in higher volume and more tone control range.

FIG. 8, FIG. 9, and FIG. 10 illustrate side views and a top view, respectively, showing more details of the inner components of the presently disclosed sound making device 100. Namely, FIG. 8 shows the sound making device 100 absent the outer acoustic shell 110 and the inner acoustic shell 120, thereby showing more details of the UI assembly 140, the fan assembly 150, and the motor mounts 134 of the base tray 130. Referring now to FIG. 9, the sound making device 100 is further absent the base tray 130, thereby showing more details of the circuit board 160, which is installed in the base tray 130. Referring still to FIG. 9, the UI circuit board 170 can be, for example, a standard printed circuit board (PCB). Three pushbutton switches 172 are mounted atop the UI circuit board 170. The first pushbutton switch 172 corresponds to the power (on/off) button 146 (see FIG. 1). The second pushbutton switch 172 corresponds to the increase volume button 147 (see FIG. 1). The third pushbutton switch 172 corresponds to the decrease volume button 148 (see FIG. 1). The UI circuit board 170 also includes certain male and/or female connectors 174 for electrically connecting to the circuit board 160 and/or the fan motor 154 (see FIG. 25). Likewise, the circuit board 160 can be, for example, a standard PCB. The circuit board 160 also includes certain male and/or female connectors 174 for electrically connecting to certain corresponding male and/or female connectors 174 on the UI circuit board 170 and/or the fan motor 154 (see FIG. 25). Referring now to FIG. 10 is a top view of the sound making device 100 absent the outer acoustic shell 110, the inner acoustic shell 120, and the UI assembly 140, thereby showing more details of the fan assembly 150 with respect to the base tray 130.

FIG. 11 illustrates perspective views showing more details of the UI assembly 140 of the presently disclosed sound making device 100. Namely, FIG. 11 shows the inner portion 142 and the UI support ring 144 arranged with respect to the UI circuit board 170. Also showing the pushbutton switches 172 of the UI circuit board 170 arranged with respect to the power (on/off) button 146, the increase volume button 147, and the decrease volume button 148. Further, a spring 176 is arranged between the power (on/off) button 146 and its corresponding pushbutton switch 172.

More details of the dome-shaped outer acoustic shell 110 are shown in FIG. 12, which contains perspective views of an example of the outer acoustic shell 110. FIG. 12 shows that the outer acoustic shell 110 includes the UI opening 114 as well as a set of alignment features or members 116 around the inner surface of the top of the outer acoustic shell 110. Namely, two large-diameter alignment features 116 and two small-diameter alignment features 116. More details of the dome-shaped inner acoustic shell 120 are shown in FIG. 13, which contains perspective views of an example of the inner acoustic shell 120. FIG. 13 shows an arrangement of alignment slots 126 around the top of the dome-shaped inner acoustic shell 120. Namely, two large-width slots 126 and two small-width slots 126. When assembled, the large-diameter alignment features 116 of the outer acoustic shell 110 are slideably engaged with the large-width slots 126 in the inner acoustic shell 120. Likewise, the small-diameter alignment features 116 of the outer acoustic shell 110 are slideably engaged with the small-width slots 126 in the inner acoustic shell 120. In doing so, the relationship of the outer acoustic shell slots 112 to inner acoustic shell slots 122 is established and ensured. Further, the UI support ring 144 of the UI assembly 140 (see FIG. 11) has certain features for snap-fitting into corresponding features of the receiver portion 124 of the inner acoustic shell 120. More details of the base tray 130 are shown in FIG. 14, which contains perspective views of an example of the base tray 130. FIG. 14 shows the opening 136 that provides access to the power port 162 of the circuit board 160. More details of the UI assembly 140 are shown in FIG. 15, which contains various views of an example of the UI assembly 140.

Each of the nine (not limiting) outer acoustic shell slots 112 of the outer acoustic shell 110 overlaps with a corresponding inner acoustic shell slot 122 of the inner acoustic shell 120. For example, a first outer acoustic shell slot 112 of outer acoustic shell 110 overlaps with a first inner acoustic shell slot 122 of the inner acoustic shell 120, a second outer acoustic shell slot 112 of outer acoustic shell 110 overlaps with a second inner acoustic shell slot 122 of the inner acoustic shell 120, and so on. The nine overlapping regions of the nine outer acoustic shell slots 112 and the nine inner acoustic shell slots 122 form nine apertures 128 (see FIG. 1, FIG. 2, FIG. 3, and FIG. 7) through which rushing air can escape. The fan assembly 150 provides a variable speed fan, which is the source of the rushing air.

With respect to producing sound mechanically via the presently disclosed sound making device 100, the outer acoustic shell 110 is rotatable with respect to the inner acoustic shell 120. That is, the inner acoustic shell 120 is held fixed within sound making device 100 while the outer acoustic shell 110 is rotatable to varying positions around the inner acoustic shell 120. The limits of the rotation is set by the alignment features 116 of the outer acoustic shell 110 that are slideably engaged with the slots 126 in the inner acoustic shell 120. By rotating the outer acoustic shell 110 with respect to the inner acoustic shell 120, the relationships of the outer acoustic shell slots 112 that overlap with the inner acoustic shell slots 122 can change. In so doing, the size (i.e., area) and/or shape of the apertures 128 can be adjusted, which affects the flow of rushing air through the apertures 128 that in turn affects the loudness and/or tone of the sound produced by the sound making device 100.

For example and referring now to FIG. 16A, FIG. 16B, and FIG. 16C, each of the outer acoustic shell slots 112 is a substantially uniformly shaped slot. By contrast, each of the inner acoustic shell slots 122 is a tapered slot. In one example, the ends of the outer acoustic shell slots 112 and the inner acoustic shell slots are rounded. The radius of the inner acoustic shell slots 122 of the inner acoustic shell 120 help produce an ideal sound. In one example, the radius of the inner acoustic shell slots 122 is about 2.24 mm at bottom slot and 3.82 mm at top slot.

The outer acoustic shell slots 112 are angled (e.g., at about 32 degrees) in one direction while the inner acoustic shell slots 122 are angled (e.g., at about 14 degrees) in the opposite direction with respect to vertical. In so doing, the outer acoustic shell slots 112 and the inner acoustic shell slots 122 are arranged in a cross configuration as exemplified in FIG. 16B.

The aperture 128 is formed at the overlap region of the outer acoustic shell slot 112 and the inner acoustic shell slot 122. By changing the position of the outer acoustic shell slot 112 with respect to the inner acoustic shell slot 122, the size (i.e., area) and/or shape of the aperture 128 can be adjusted. For example, FIG. 16A shows the outer acoustic shell slot 112 overlapping at about the widest portion of the inner acoustic shell slot 122 to form a large sized aperture 128. FIG. 16B shows the outer acoustic shell slot 112 overlapping at about a midway portion of the inner acoustic shell slot 122 to form a middle sized aperture 128. FIG. 16C shows the outer acoustic shell slot 112 overlapping at about the narrowest portion of the inner acoustic shell slot 122 to form a small sized aperture 128. Also note that both the geometry or shape and the size (i.e., area) of the aperture 128 changes, which affects the acoustics of the airflow therethrough.

FIG. 17 illustrates a block diagram of an example of a sound making system 200 that includes the presently disclosed sound making device 100 in combination with a mobile app. The sound making device 100 includes a controller 210, a user interface 218, a variable speed fan 220, and a power source 222. Additionally, the controller 210 can include a communications interface 216. Optionally, the communications interface 216 can be provided separate from the controller 210 rather than built in. In one example, the controller 210 is provided on the UI circuit board 170 of the sound making device 100. The UI assembly 140 of the sound making device 100 is an example of the user interface 218 shown in FIG. 17. The fan assembly 150 of the sound making device 100 is an example of the variable speed fan 220 shown in FIG. 17. The circuitry of the circuit board 160 of the sound making device 100 is an example of the power source 222 shown in FIG. 17.

Additionally, the sound making device 100 can include voice control 224, wherein the voice control 224 supports capability for communicating using voice-based personal assistant technology, such as, but not limited to, technology developed by Amazon (e.g.; the Amazon Echo and Amazon Echo Dot devices), Google (e.g., the Google Home device), and/or Apple (e.g., Siri on the iPhone).

The variable speed fan 220 (or fan assembly 150) can include, for example, a brushless DC motor, RPM range up to, for example, about 4000 RPM, variable speed via pulse width modulation (PWM) or voltage control, and with speed increments, for example, of 0-10.

The controller 210 can be any standard controller or microprocessor device that is capable of executing program instructions. The controller 210 manages the overall operations of the sound making device 100. In one example, the controller 210 is based on the programmable 8051 processor. However, the programmable 8051 processor is exemplary only. Any processor can be used.

The communications interface 216 may be any wired and/or wireless communication interface for connecting to a network (not shown) and by which information may be exchanged with other devices connected to the network. Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, cellular network, ISM, Bluetooth® technology, Bluetooth® Low Energy (BLE) technology, Wi-Fi, Wi-Max, IEEE 402.11 technology, ZigBee technology, Z-Wave technology, 6LoWPAN technology (i.e., IPv6 over Low Power Wireless Area Network (6LoWPAN)), ANT or ANT+ (Advanced Network Tools) technology, radio frequency (RF), Infrared Data Association (IrDA) compatible protocols, Local Area Networks (LAN), Wireless Local Area Networks (WLAN), Wide Area Networks (WAN), Personal Area Networks (PAN), Shared Wireless Access Protocol (SWAP), any combinations thereof, and other types of wireless networking protocols.

In one example, the communications interface 216 is Bluetooth® technology for communicating with a mobile app on a mobile device. For example, associated with the sound making system 200 is one or more users 240. The user 240 has one or more computing devices 250 that can be used to communicate with the sound making device 100. In this example, the computing devices 250 can be any Bluetooth-enabled computing device, such as, but not limited to a tablet device, a mobile phone, a smartphone, a smartwatch, a voice-based personal assistant, and the like. A sound making app 252 is running on the computing device 250. The sound making app 252 can be, for example, for Android and iOS. In one example, the computing device 250 vibrates, makes a sound, and/or provides a visual indicator when paired with the sound making device 100.

Using the sound making app 252, information can be exchanged in wireless fashion (e.g., using the Bluetooth® technology) between the sound making device 100 and the computing device 250. The sound making app 252 has capability to process and display any information from the sound making device 100.

In operation, the sound making device 100 can be operated either manually from the user interface 218, the sound making app 252, and/or voice-based personal assistant technology, such as Amazon Alexa. In any case, the basic functions may include, for example, turning the power off/on and volume control (i.e., 0-10 speed increments of the fan). However, other functions are possible using the sound making app 252. For example, using the sound making app 252, multiple sleep schedules can be set up. Each sleep schedule can include an off/on time based on time/date inputs and a volume setting. The sound making device 100 can be designed to remember user schedules through short term power loss. The sound making device 100 can be designed such that the manual buttons on the user interface 218 can override the settings of the sound making app 252. Additionally, tutorials may be programmed into the controller 210 to assist with user setup. Further, the controller 210 of the sound making device 100 may have the ability to push notifications to the user.

Further, a sleep coaching feature may be programmed into the controller 210 of the sound making device 100. The sleep coaching feature may be anything that offers better sleep recommendations. For example, it may be recommended to keep the sound making device 100 turned on setting 5 through the first 2 weeks. Then at week 2, the user 240 is notified that they have adjusted to the sound and can turn up the volume if needed (or something similar).

Referring again to FIG. 1 through FIG. 17, the features of the presently disclosed sound making device 100 and sound making system 200 that includes the sound making app 252 include, but are not limited to, the following.

1) The sound making device 100 is a sound emitting machine that produces a soothing white noise, wherein the unique sound frequencies are reached through the acoustically engineered combination of the DC motor, fan blades, and enclosure housing (i.e., the outer acoustic shell 110, the inner acoustic shell 120, and the base tray 130).
2) The sound making device 100 provides real and adjustable white noise for sound screening for privacy and a soothing sound for those using it for sleep.
3) The sound making device 100 is a portable sound conditioner that includes a DC motor, variable speed controller, external power supply, and sophisticated fan blade design for blocking out background noise.
4) The sound making device 100 provides fully adjustable tone and sound.
5) The sound making app 252 of the sound making system 200 provides increased variability and remote usage of the sound making device 100.
6) The radius of the inner acoustic shell slots 122 of the inner acoustic shell 120 help produce an ideal sound. In one example, the radius of the inner acoustic shell slots 122 is about 2.24 mm at bottom slot and 3.82 mm at top slot.

Figure 18:
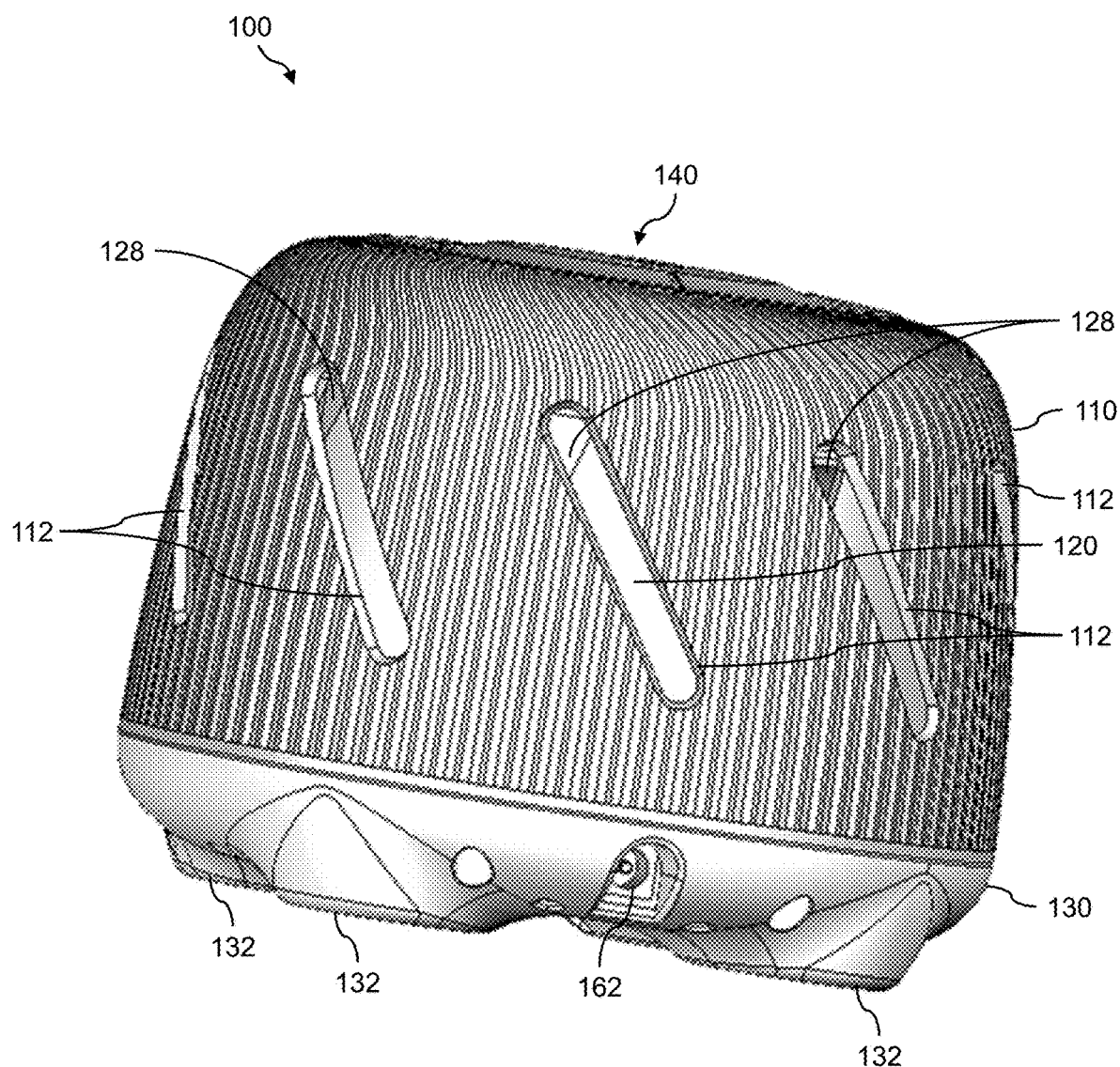
Figure 19:
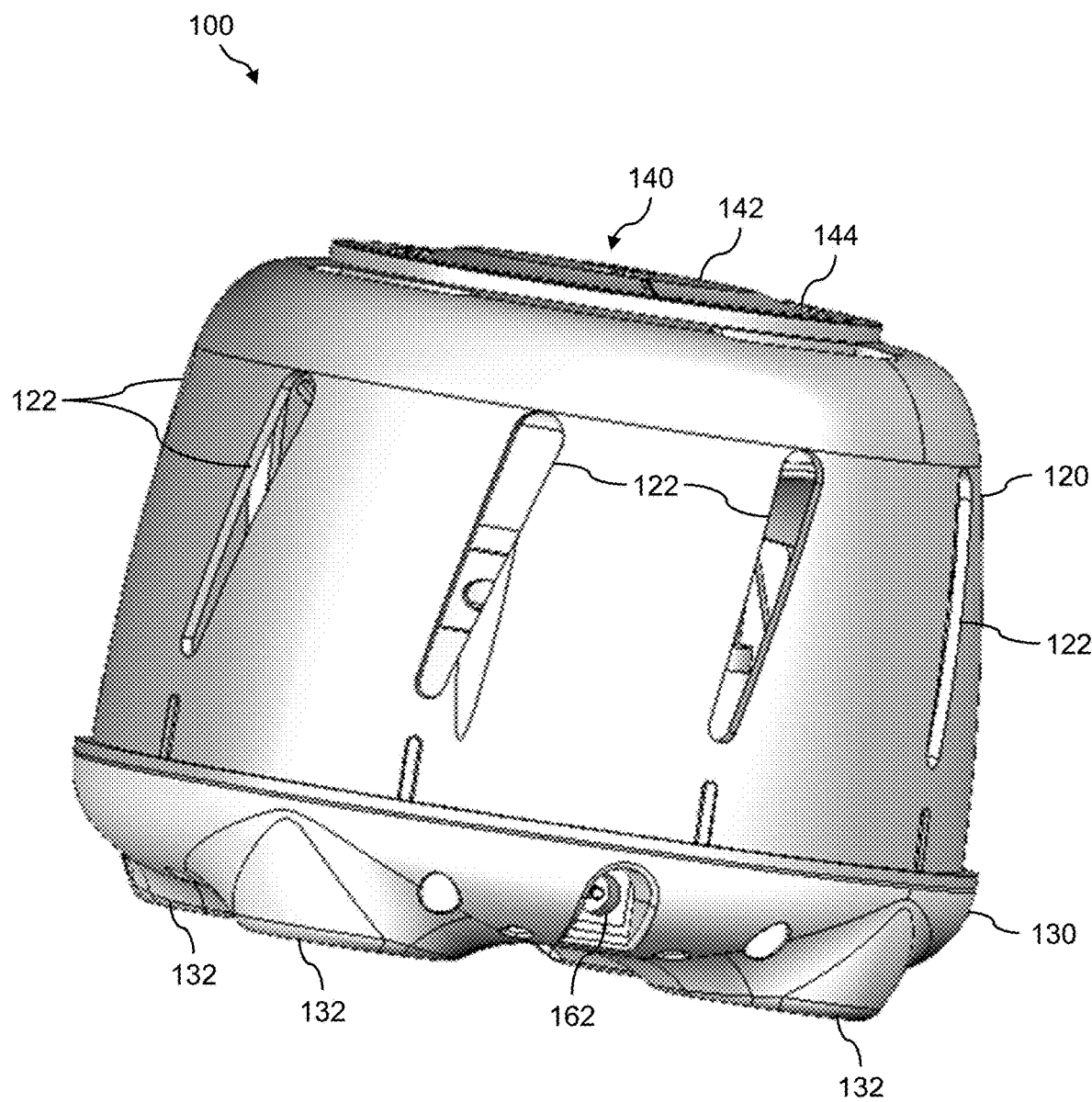
Figure 20:
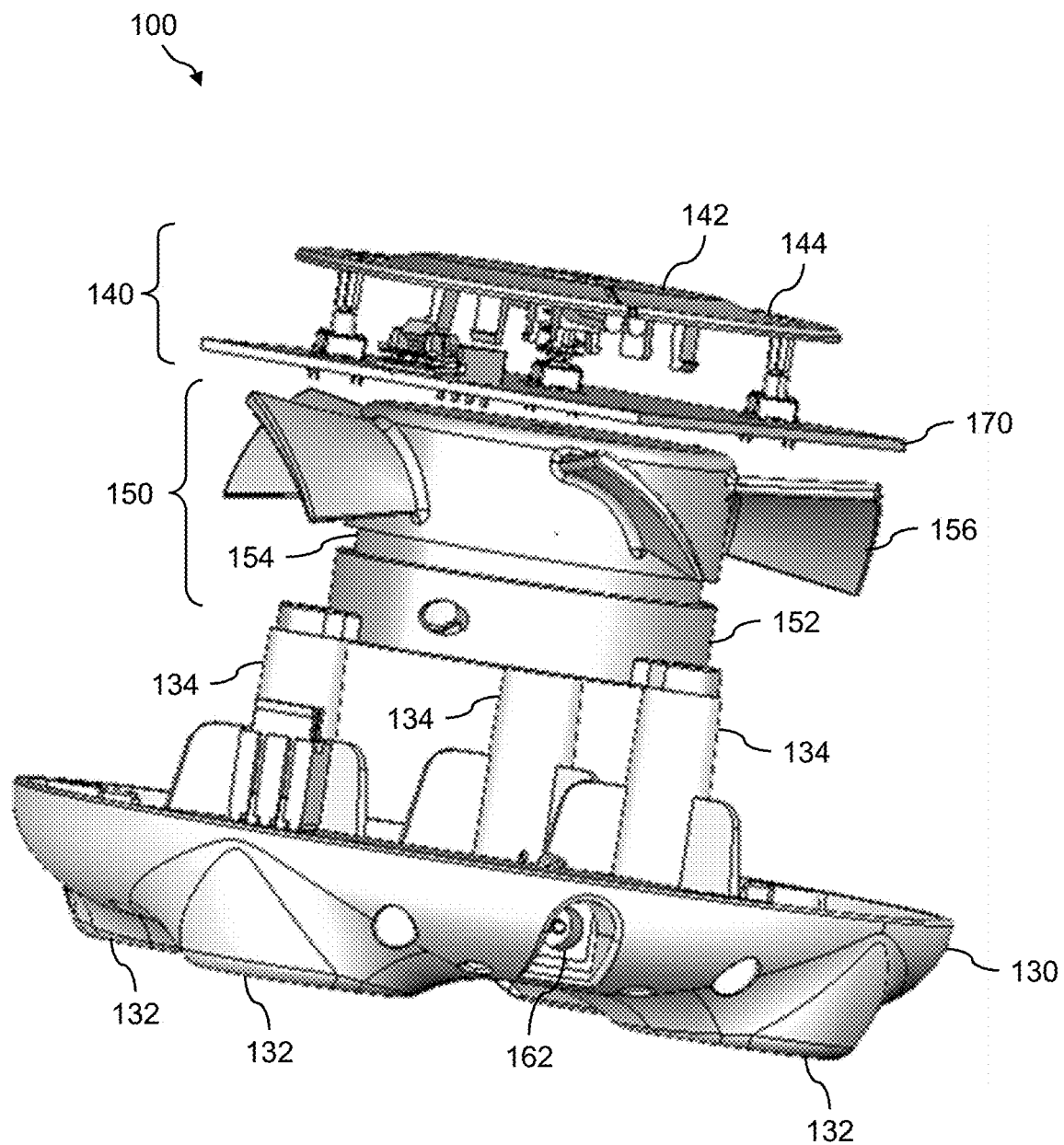
Figure 21:
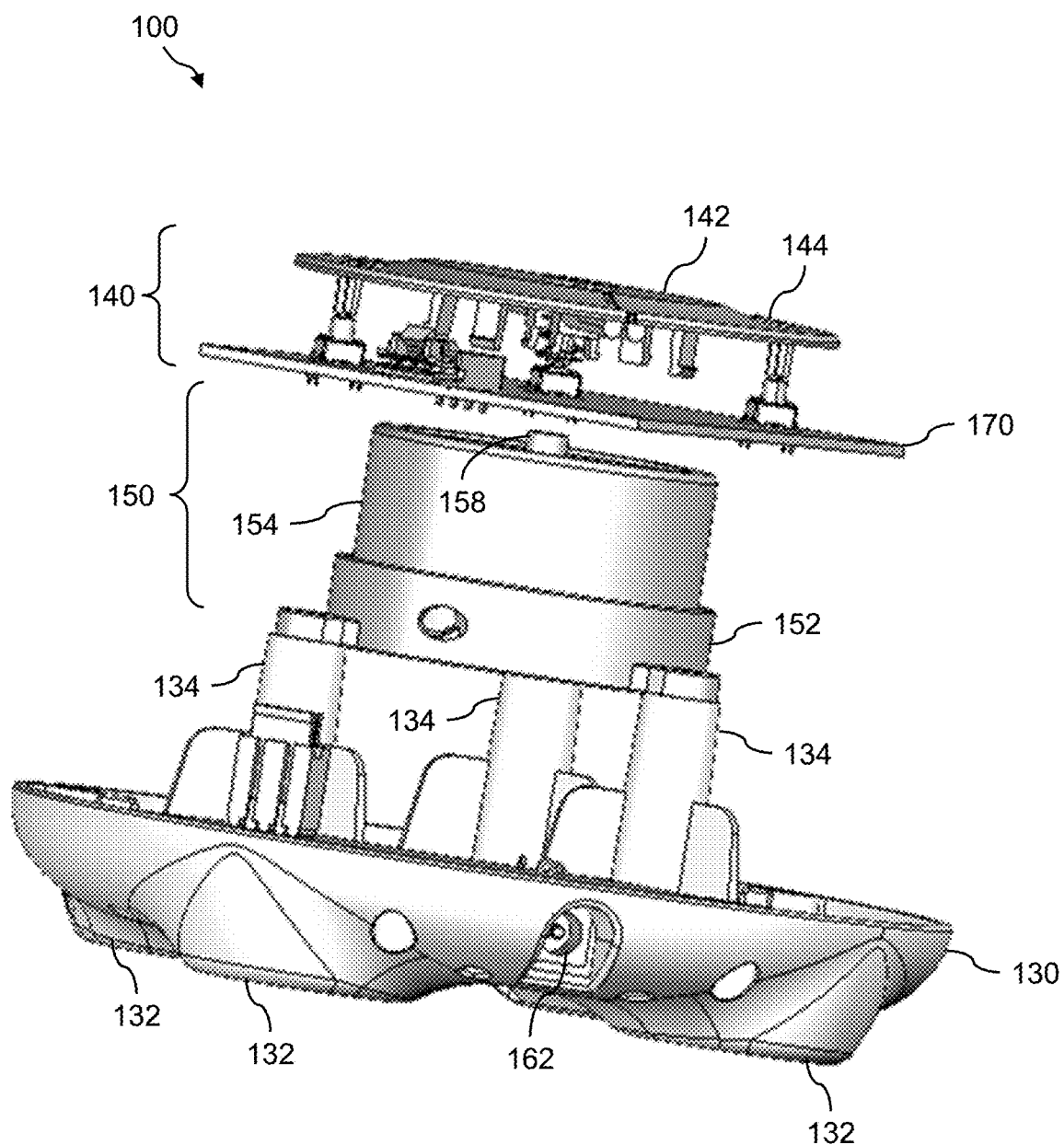
Figure 22:
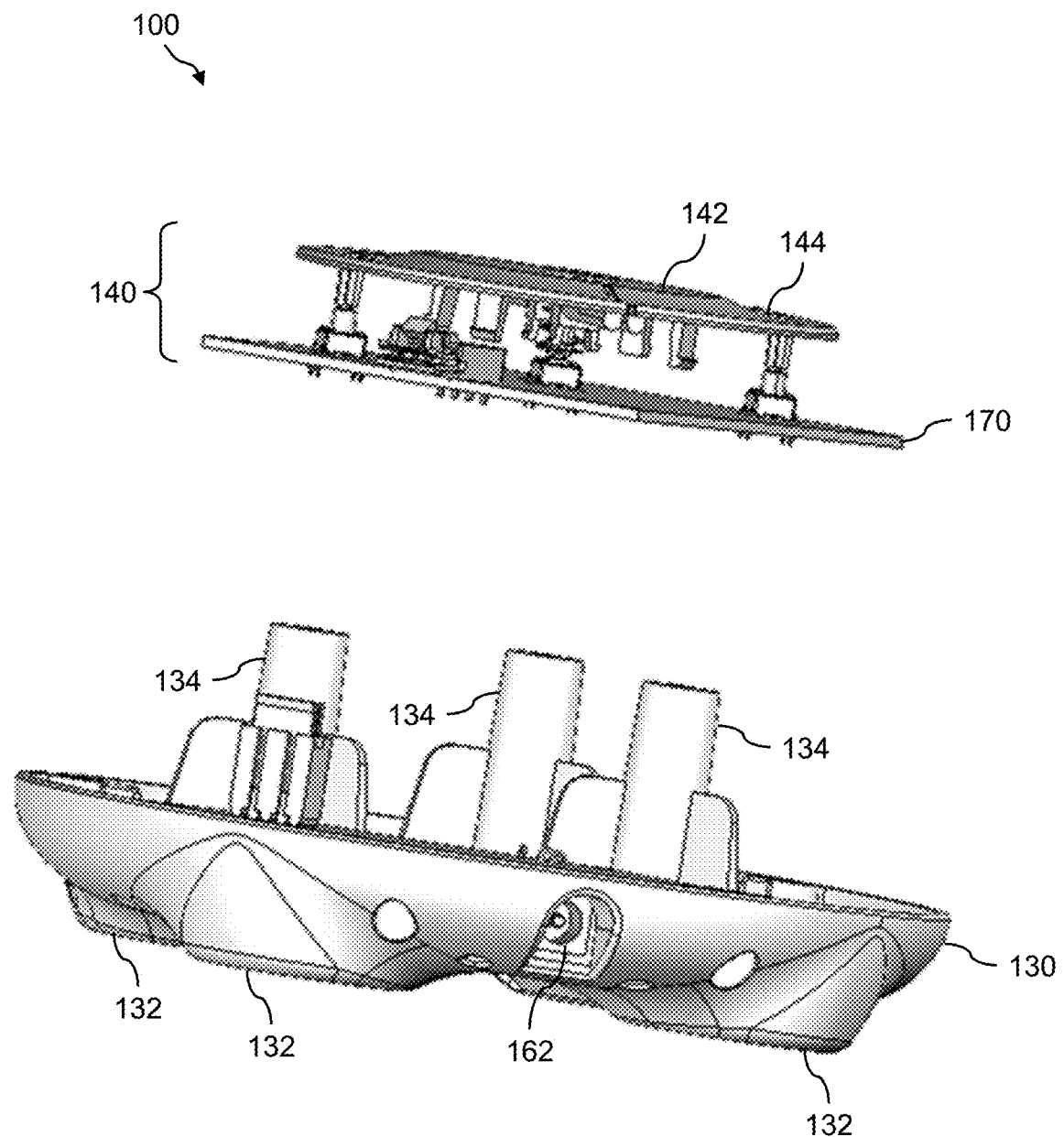
Figure 23:
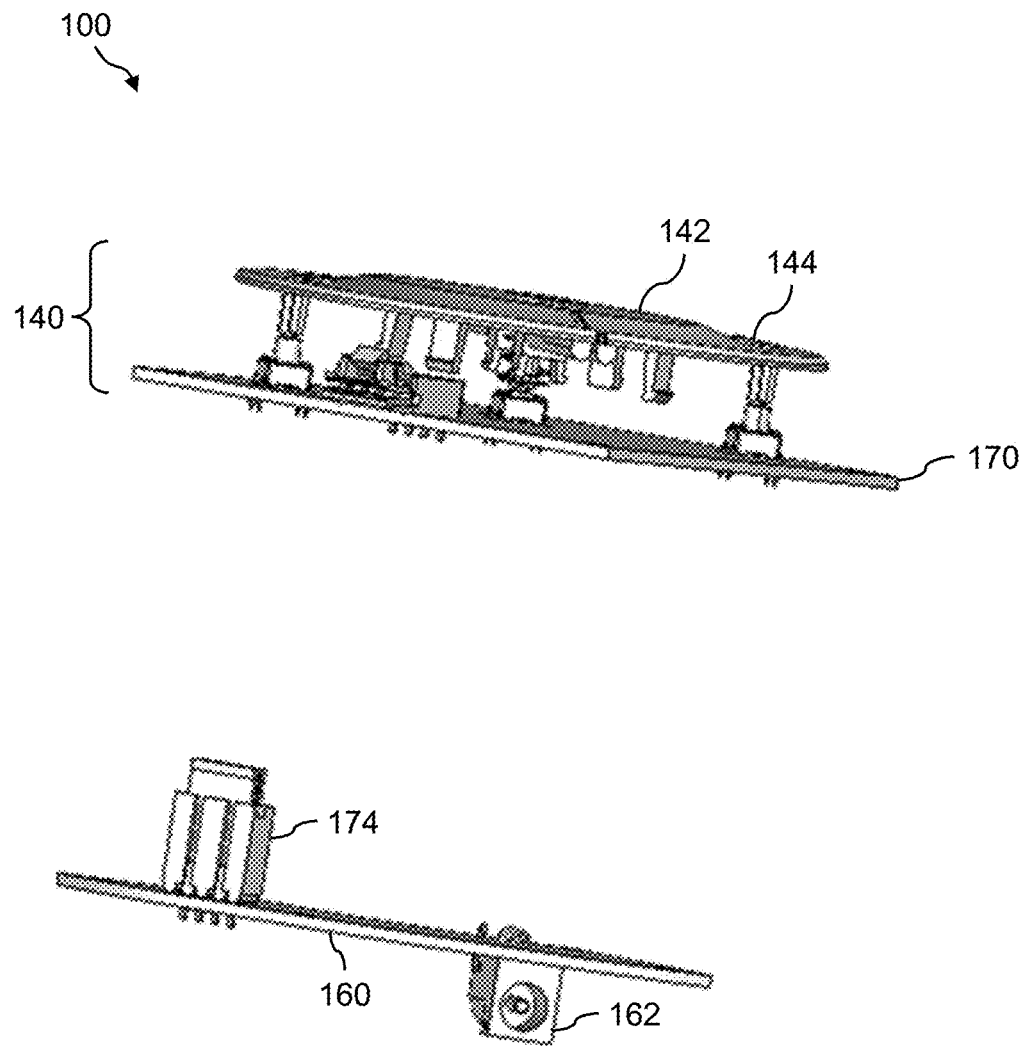
Figure 24:
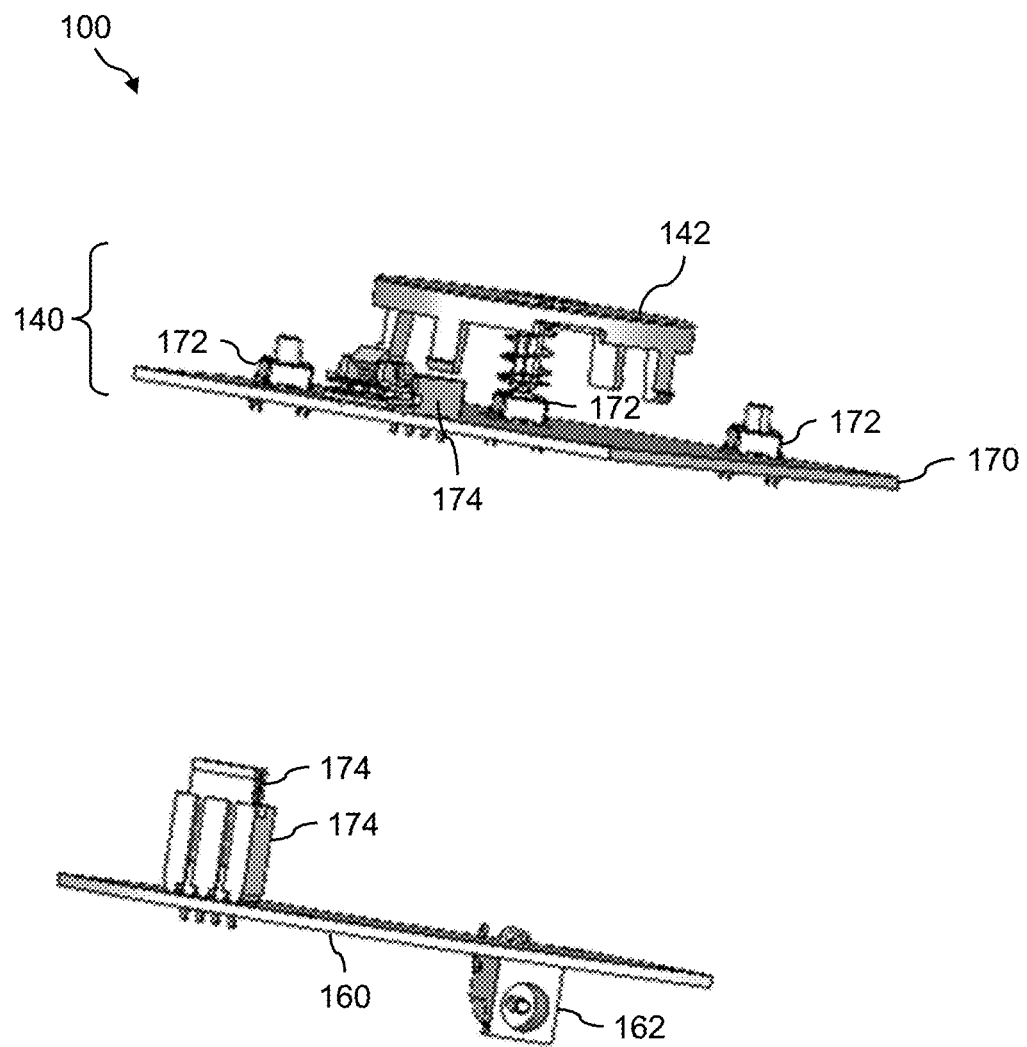
Figure 25:
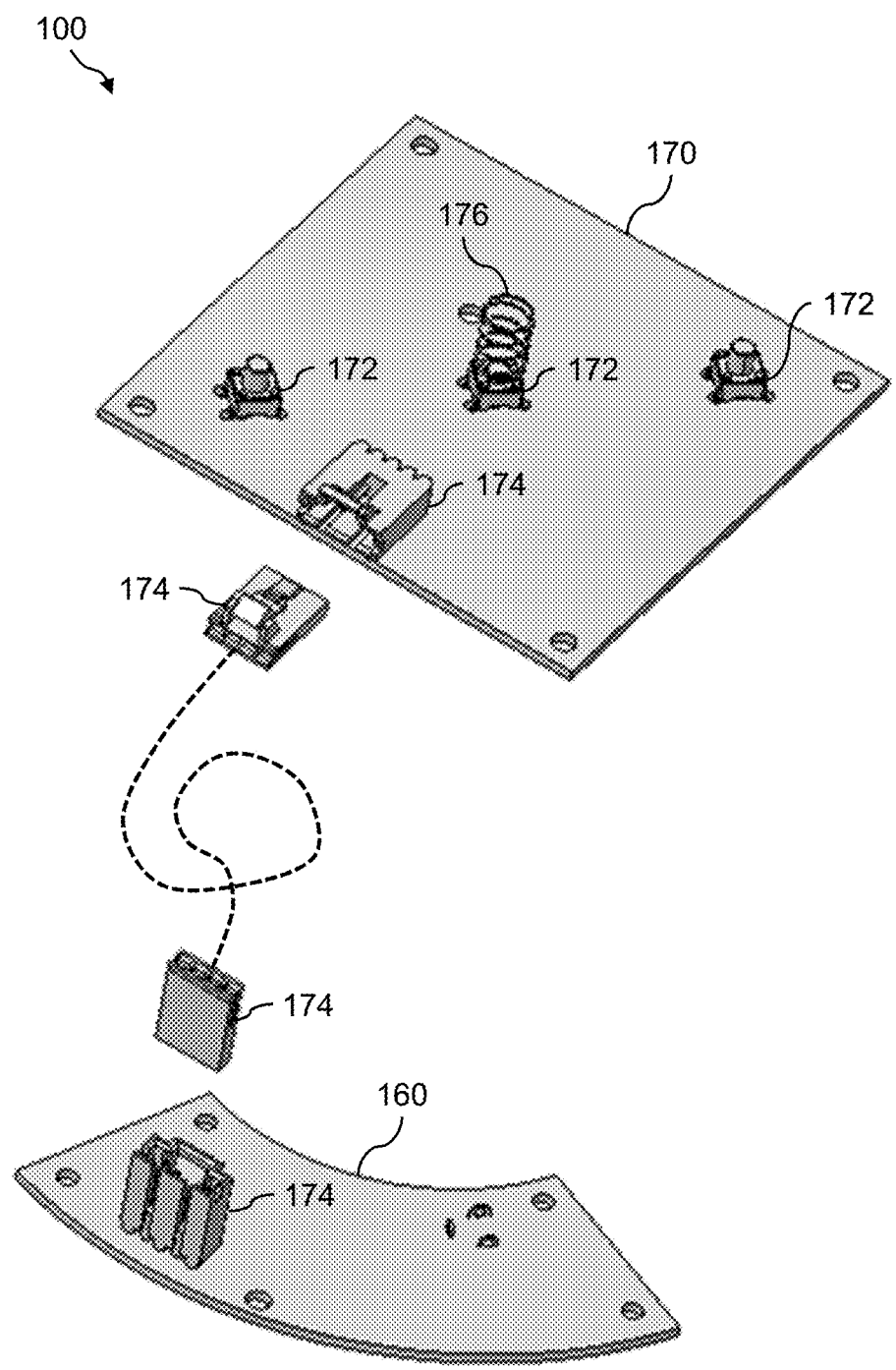

FIG. 18 through FIG. 25 is a series of views showing the deconstruction of the presently disclosed sound making device 100 and incrementally revealing the components thereof. For example, FIG. 18 shows a perspective view of the sound making device 100 in its entirety. FIG. 19 shows the sound making device 100 absent the outer acoustic shell 110 and thereby revealing the inner acoustic shell 120. FIG. 20 shows the sound making device 100 further absent the inner acoustic shell 120 and thereby revealing the fan assembly 150 and the UI assembly 140. FIG. 21 shows the sound making device 100 further absent the fan blade 156 and thereby revealing more details of the fan assembly 150. FIG. 22 shows the sound making device 100 further absent the entirety of the fan assembly 150 and thereby revealing more details of the base tray 130 including the motor mounts 134. FIG. 23 shows the sound making device 100 further absent the base tray 130 and the fan assembly 150 and thereby revealing more details of the circuit board 160. FIG. 24 shows the sound making device 100 further absent the UI support ring 144 of the UI assembly 140 and thereby revealing more details of the UI circuit board 170. FIG. 25 shows a perspective view of the circuit board 160 and the UI circuit board 170 and showing more details of the pushbutton switches 172, the male and/or female connectors 174 for electrically connecting the circuit board 160 to the UI circuit board 170, and the spring 176.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the present subject matter.

We claim:

1. A sound making device for generating white noise, comprising:
   a) an enclosure housing having an outer acoustic shell and an inner acoustic shell mounted atop a base tray, the outer acoustic shell having a set of outer acoustic shell slots and the inner acoustic shell having a set of inner acoustic shell slots, the outer acoustic shell slots and the inner acoustic shell slots overlapping to form a set of apertures through which air can pass, wherein the set of outer acoustic shell slots are arranged around the sides of the outer acoustic shell and angled in one direction, wherein the set of inner acoustic shell slots are arranged around the side of the inner acoustic shell and angled in a direction opposite to the one direction, the set of outer acoustic shell slots and the set of inner acoustic shell slots being in a cross configuration;
   b) a fan assembly inside the enclosure including a variable speed fan and a fan motor for forcing the air out of the apertures; and
   c) a controller and a user interface assembly for controlling the speed of the variable speed fan.

2. The sound making device as in claim 1, wherein the enclosure is substantially dome-shaped.

3. The sound making device as in claim 2, wherein the outer acoustic shell is dome-shaped, and wherein the inner acoustic shell is dome-shaped.

4. The sound making device as in claim 3, wherein the inner acoustic shell is fixed, and wherein the outer acoustic shell is rotatable to varying positions around the inner acoustic shell.

5. The sound making device as in claim 4, wherein the shape of each aperture of the set of apertures is adjustable according to the position of the rotatable outer acoustic shell in relation to the fixed inner acoustic shell.

6. The sound making device as in claim 5, wherein the outer acoustic shell includes a user interface opening for receiving the user interface assembly and a set of large-diameter alignment features and a set of small-diameter alignment features around the inner surface of the outer acoustic shell.

7. The sound making device as in claim 6, wherein the inner acoustic shell includes a set of large-width alignment slots and a set of small-width alignment slots around the top of the inner acoustic shell, the set of large-width alignment slots and the set of large-diameter alignment features being slideably engaged, and the set of small-width alignment slots and the set of small-diameter alignment features being slideably engaged.

8. The sound making device as in claim 1, wherein the outer acoustic shell is rotatable with respect to the inner acoustic shell.

9. The sound making device as in claim 1, wherein each slot of the set of outer acoustic shell slots is a substantially uniformly shaped slot, and wherein each slot of the set of inner acoustic shell slots is a tapered slot.

10. The sound making device as in claim 1, wherein the user interface assembly includes an inner portion arranged with respect to user interface support ring surrounding the inner portion, and a user interface circuit board, the inner portion supporting a power button, and the user interface support ring support an increase volume button and a decrease volume button.

11. The sound making device as in claim 10, wherein the inner acoustic shell includes an upper receiver portion for supporting the user interface assembly, the user interface support ring being mounted above and coupled to the receiver portion, the user interface circuit board being mounted below and coupled to the receiver portion, the user interface circuit board having a first pushbutton switch corresponding to the power button, a second pushbutton switch corresponding to the increase volume button, and a third pushbutton switch corresponding to the decrease volume button.

12. The sound making device as in claim 1, wherein the fan assembly is held by the base tray, the base tray including a motor mount, the fan assembly including a motor support for mounting to the motor mount and for holding the fan motor, the fan motor having a motor shaft, the variable speed fan having a fan blade, wherein the fan blade is mounted on the motor shaft.

13. The sound making device as in claim 12, further comprising a power circuit board for receiving DC voltage and to provide a voltage regulation function for powering the fan motor and the user interface assembly, the power circuit board including a power port, the power circuit board being installed in the base tray, and the base tray including an opening along an outer edge of the base trade to provide access to the power port.

14. The sound making device as in claim 12, wherein the outermost edge of the fan blade is a distance D from the inside surface of the inner acoustic shell, and wherein the fan blade is located at a height with respect to the set of inner acoustic shell slots.

15. The sound making device as in claim 14, wherein the distance D is between about 0.25 inches and about 0.625 inches.

16. The sound making device as in claim 14, wherein the height is about midway to about the top of the set of inner acoustic shell slots.

17. A sound making system for generating white noise, comprising:
   a) a sound making device having an enclosure housing having an outer acoustic shell and an inner acoustic shell mounted atop a base tray, the outer acoustic shell having a set of outer acoustic shell slots and the inner acoustic shell having a set of inner acoustic shell slots, the outer acoustic shell slots and the inner acoustic shell slots overlapping to form a set of apertures through which air can pass, wherein the set of outer acoustic shell slots are arranged around the sides of the outer acoustic shell and angled in one direction, wherein the set of inner acoustic shell slots are arranged around the side of the inner acoustic shell and angled in a direction opposite to the one direction, the set of outer acoustic shell slots and the set of inner acoustic shell slots being in a cross configuration, a fan assembly inside the enclosure including a variable speed fan and a fan motor for forcing the air out of the apertures, a controller to manage the overall operations of the sound making device, a user interface assembly for manual operation of the sound making device, and a power source for powering the sound making device; and b) a mobile app for using the sound making device.

18. The sound making system as in claim 17, further comprising a communications interface for communicating with the mobile app, and a voice control for communicating with a voice-based personal assistant.

19. The sound making system as in claim 18, further comprising a computing device, the mobile app adapted to exchange information between the sound making device and the computing device.

\* \* \* \* \*